US006893716B2

(12) United States Patent
McGimpsey et al.

(10) Patent No.: US 6,893,716 B2
(45) Date of Patent: May 17, 2005

(54) NON-COVALENT ASSEMBLY OF MULTILAYER THIN FILM SUPRAMOLECULAR STRUCTURES

(75) Inventors: William Grant McGimpsey, Boylston, MA (US); John C. MacDonald, Jefferson, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 10/681,835

(22) Filed: Oct. 7, 2003

(65) Prior Publication Data

US 2004/0110009 A1 Jun. 10, 2004

Related U.S. Application Data

(60) Provisional application No. 60/416,511, filed on Oct. 7, 2002.

(51) Int. Cl.[7] .............................. B32B 9/00; B32B 33/00
(52) U.S. Cl. ...................... 428/333; 428/338; 428/411.1
(58) Field of Search ................................. 428/333, 338, 428/411.1

(56) References Cited

U.S. PATENT DOCUMENTS

| 5,536,573 A | 7/1996 | Rubner et al. |
| 6,107,561 A | 8/2000 | Thompson |
| 6,114,099 A | 9/2000 | Liu et al. |
| 6,270,946 B1 | 8/2001 | Miller |
| H2046 H | 9/2002 | Roberts et al. |
| 6,451,871 B1 | 9/2002 | Winterton et al. |

OTHER PUBLICATIONS

Hun–Gi Hong et al., "Electrochemical Measurements of Electron Transfer Rates through Zirconium 1,2–Ethanediyl-bis (phosphonate) Multilayer Films on Gold Electrodes", Langmuir, 7:2362–2369 (1991).

M. Brust et al., "Self–Assembly of Photoluminescent Copper(I)–Dithiol Multilayer Thin Films and Bulk Materials", Langmuir, 13:5602–5607 (1997).

A. Hatzor et al., "Coordination–Controlled Self–Assembled Multilayers on Gold", J.Am.Chem.Soc., 120:13469–13477 (1998).

H. Imahori et al., "Chain Length Effect on the Structure and Photoelectrochemical Properties of Self–Assembled Monolayers of Porphyrins on Gold Electrodes", J.Phys.Chem. B, 104:1253–1260 (2000).

(Continued)

*Primary Examiner*—Ramsey Zacharia
(74) *Attorney, Agent, or Firm*—R. Dennis Creehan, Esq.

(57) ABSTRACT

Self-assembled monolayers and multilayer thin film structures were assembled from multiple components that were linked non-covalently by metal-ligand complexation. Non-covalently assembled multicomponent films assembly my the present method obviate problems associated with the covalent assembly of SAMs and multilayer thin film structures from large molecules. In one preferred embodiment, the disclosed film structures comprise 2,6 pyridinedicarboxylate ligands attached to an alkanethiol, which form a self-assembled monolayer on gold. The SAM is subsequently functionalized by sequential deposition of metal ions and ligands, allowing incorporation of one or more chromophores, photooxiding compounds or photoreducing to form multilayer film structures. Transition metals, lanthanide metals and other metals of varying charge may be employed in complexing with with 2,6 pyridinedicarboxylate ligands to form stable ordered structures. The non-covalent assembly method provides for multilayer film formation from mixtures of metal ions and a varying number of film layers. Multilayer thin film structures exhibit stable cathodic photocurrent generation in the presence of methyl viologen or EDTA in solution.

2 Claims, 7 Drawing Sheets

OTHER PUBLICATIONS

J.C. MacDonald et al., "Design of Layered Crystalline Materials Using Coordination Chemistry and Hydrogen Bonds", J.Am.Chem.Soc., 122:11692–11702 (2000).

H. Imahori et al., "Concentration Effects of Porphyrin Monolayers of the Structure and Photoelectrochemical Properties of Mixed Self–Assembled Monolayers of Porphyrin and Alkanethiol on Gold Electrodes", Langmuir, 17:4925–4931 (2001).

H. Imahori et al., "Light–Harvesting and Photocurrent Generation by Gold Electrodes Modified with Mixed Self–Assembled Monoloyers of Boron–Dipyrrin and Ferrocene–Porphyrin–Fullerene Triad", J.Am.Chem.Soc., 123:100–110 (2001).

D. Hirayama et al., "Large Photocurrent Generation of Gold Electrodes Modified with [60]Fullerene–Linked Oligothiophenes Bearing a Tripodal Rigid Anchor", J.Am.Chem.Soc., 124(4):532–533.

F.B. Abdelrazzaq et al., "Photocurrent Generation in Multilayer Organic–Inorganic Thin Films with Cascade Energy Architectures", J.Am.Chem.Soc., 124:4796–4803 (2002).

E. Soto et al., "A Non–Covalent Strategy for the Assembly of Supramolecular Photocurrent–Generating Systems", J.Am.Chem.Soc., 125:2838–2839 (2003).

C. Lin et al., "Layer–By–Layer Growth of Metal–Metal Bonded Supramolecular Thin Films and Its Use in the Fabrication of Lateral Nanoscale Devices", J.Am.Chem.Soc., 125:336–337 (2003.

Pyrene

Porphyrin

NON-COVALENT ASSEMBLY OF MULTILAYER THIN FILM SUPRAMOLECULAR STRUCTURES

CROSS-REFERENCES

This application claims the benefit under 35 U.S.C. 119(e) of U.S. provisional patent application U.S. Ser No. 60/416,511 filed on Oct. 7, 2002 which is incorporated herein by this reference.

FIELD OF THE INVENTION

This invention relates generally to thin film, multilayer, supramolecular structures coupled to surfaces and methods for their fabrication. More particularly, this invention relates self-assembled monolayers and mutilayered thin film systems where photoactive film layers are non-covalently coupled to surfaces and multilayer structures are non-covalently assembled by sequential deposition of metal-ligand complexes.

BACKGROUND OF THE INVENTION

Natural photosynthetic systems are fairly sophisticated natural molecular assemblies which consist of aggregates of chlorophylls and carotenoids that absorb light to intiate a sequence of energy transport steps. Fabrication of artificial photosynthetic systems which can generate current upon photoexcitation with the same high efficiency of conversion as occurs in natural photosynthetic systems would be particularly advantageous. Organized artificial molecular assemblies are of potential use in the design of efficient devices for photoenergy conversion, photocurrent generation and photoswitching or for devices such as molecular wires and switches. Design of a highly efficient artificial photosynthetic system requires the efficient and reproducable organization of photon harvesting groups, electron donors and electron acceptors into a molecular assembly that facilitates the conversion of light into electrical current and chemical potential with high efficiency. While some workers have explored prototype supramolecular structures for such applications, to date many of these artificial systems have exhibit problems with their stability and efficiency of energy conversion.

Self-assembled monolayers (SAMs) are particularly attractive for fabrication of artificial photosynthetic system by constructing molecular assemblies with light harvesting groups on top of the monolayers. The light harvesting and charge separation character of the monolayers is evidenced by the generation of current upon photoexcitation of the SAM in the presence of an electron donor or electron acceptor compound. The basic idea for preparation of these devices is to attach a molecule, for example an alkanethiol, with a chromophore group placed on top of the layer, so as to be easily exposed on the surface and therefore to be able to absorb light from an external source and to start the photocurrent flow through the system. An example of this type of devices is given in the work by Imahori (H. Imahori et al., *J. Phys. Chem. B* 2000, 104, 1253–1260) who uses phorphyrins coupled to long chain alkanethiols to produce photocurrent. Other compounds, such as peptides have also been used because they facilitate electron transfer from the gold surface to the chromophore. Kimura, et. al. (T. Morita et al., *J. Am. Chem. Soc.* 2000, 122, 2850–2859) were the first to report the use of peptide SAMs for photocurrent generation. The choice of peptide backbones was based on the electrostatic field that helical peptides possess. Fox et al. (*J. Am. Chem. Soc.* 1997, 119, 5277–5285; *J. Phys. Org. Chem.*, 1997, 10, 484–498; *J. Am. Chem. Soc.*, 1996, 118, 2299–2300.) and Imanishi et al. (*J. Phys. Chem.* 1991, 95, 3847–3851) have shown that this electric field can favored the rate of electron transfer between donor-acceptor pairs located along the peptide helix.

A more complex system proposed in the work by Uosaki, et. al. (*J. Am. Chem. Soc.* 1997, 119, 8367–8368; *Thin Solid Films.* 1996, 284–285, 652–655; *Journal of Electroanalytical Chemistry.* 1997, 438, 121–126) is a SAM with a photoactive group on top and an electron relay group at the middle part of the molecule to facilitate electron transfer through the monolayer. Uosaki's group has reported many of these devices using thiol molecules containing groups such as porphyrin-ferrocene-thiol and porphyrin-mercaptoquinone systems. The presence of an electron relay group, of lower oxidation potential than the electroactive unit, favors the electron transfer from the gold surface towards the electroactive compound (cathodic photocurrent) or from the excited singlet state of the electroactive compound towards the gold surface (anodic photocurrent). The cathodic photocurrent is enhanced with more negative potentials applied to the working electrode, and the anodic with more positive potentials.

An even more sophisticated system has been designed by Imahori et. al. (*J. Am. Chem. Soc.* 2001, 123, 100–110; *Chem. Commun.* 2000, 661–662). Their systems consist of mixed monolayers with different chromophore groups on top, one of them to serve as antenna and enhance the photocurrent generation by energy transfer to the second chromophore. The first system described by Imahori has pyrene and porphyrin molecules. The photocurrent is enhanced by an energy transfer from the pyrene to the porphyrin. A more complex system contains a boron-dipyrrin molecule as an antenna complex and a molecule bearing a ferrocene, porphyrin and [60]fullerene. With this system, the photocurrent is produced from the gold towards the fullerene by using the ferrocene as electron relay group and porphyrin as the photoexcited molecule. The boron-dipyrrin molecule enhances the photocurrent by energy transfer to the porphyrin.

Besides complex organic molecules, other possibility for preparation of supramolecular devices is the use of metals inside the SAM structure. Some studies have been published related to the use of metals as complexing units between different organic ligands to produce multilayers and the subsequent characterization of these systems. Bard, et. al. (*Langmuir.* 1997. 13, 5602–5607) have used copper to produce photo-luminescent multilayer thin films formed by Cu (I) sandwiched between the carboxyl and thiol groups of bifunctional molecules such as 3-mercaptopropanoic acid. Mallouk et al. (*Langmuir.* 1991, 7, 2362–2369) have reported preparation of zirconium 1,2-ethanediylbis (phosphonate) multilayer films on gold and studied the electron transfer rates through the film by electrochemical measurements. Hatzor et al. (*J. Am. Chem. Soc.* 1998, 120, 13469–13477) studied self-assembled multilayers on gold formed with zirconium, cerium and titanium ion complexes with dihydroxamate ligands. Fabrication of organic-inorganic thin films has also been reported recently by Thompson, et. al.(*J. Am. Chem. Soc.* 2002, 124, 4796–4803) and Ulman, et. al. (*Langmuir.* 2002, 18, 6207–6216). These workers have shown that organometallic multilayered systems are a convenient alternative for fabrication of stable model surfaces with potential applications in photocurrent generating systems and chemical sensing. These workers have shown that multilayer films can be grown by sequential deposition of layers and theri formation can be monitored with characterization techniques such as ellipsometry and cyclic voltammetry.

Imahori et al. (H. Imahori et al., S. *Chem. Commun.* 2000, 661–662; H. Imahori et al., *J. Phys. Chem. B* 2000, 104, 1253–1260; H. Imahori et al., *J. Am. Chem. Soc.* 2001, 123, 100–110) have fabricated self-assembled monolayers (SAMs) on gold by depositing a covalently-linked, multi-component molecule containing alkanethiol, ferrocene, porphyrin and $C_{60}$ subunits. These SAMs have both light harvesting and charge separation character as evidenced by the generation of current upon photoexcitation of the SAM in the presence of methyl viologen. Fox et al. have investigated optical and electrochemical properties of SAMs in which pyrene chromophores are coupled to gold surfaces. (M. A. Fox et al., *Langmuir* 1998, 14, 816–820; R. S. Reese and M. A. Fox, *Can. J. Chem.* 1999, 77, 1077–1084. In separate work, Mallouk et al. (H. G. Hong and T. E. Mallouk, T. E. *Langmuir* 1991, 7, 2362–2369; H. C. Yang et al., *J. Am. Chem. Soc.* 1993, 115, 11855–11862), Bard (S. Ogawa et al, A. J. *J. Phys. Chem. B* 1997, 101, 5707–5711; M. Brust et al., *Langmuir,* 1997, 13, 5602–5607) and others have studied the formation of multilayer, multicomponent thin films on gold via non-covalent interactions between sulfur-containing ligands and metal ions. In one study, Bard et al. (*Langmuir,* 1997, 13, 5602–5607) reported thin films produced by the repeated sequential deposition of mercaptoalkanoic acids and Cu(II) ions. Kimura and co-workers (T. Morita et al., *Bull. Chem. Soc. Jpn.* 2000, 73, 1535–1540; T. Morita et al., *J. Am. Chem. Soc.* 2000, 122, 2850–2859) also observed photocurrent generation following excitation of a SAM on gold that consists of an alkanethiol linked covalently to a helical peptide containing a carbazole group at the terminal residue. While the photocurrent generating efficiency reported for these systems was promising, the synthetic effort involved in producing such multifunctional molecules was likely considerable.

Incorporation of molecular components for light harvesting and charge separation into artificial photosynthetic systems requires addition structures which exhibit high harvesting efficiencies and provided for straightforward synthesis of multilayer films. While many organic systems have been developed that exhibit reasonable light harvesting efficiencies and much has been learned about the energy transfer, electron transfer and charge separation processes that occur during photosynthesis, creating a system that can efficiently convert photons to electrons remains a primary objective and unrealized goal. Of primary concern is the creation of a highly organized supramolecular scaffold that optimizes light harvesting efficiency and transfer rates which are available with the protein framework found in natural photosynthetic systems.

SUMMARY OF THE INVENTION

In the present invention, fabrication of novel photocurrent-generating systems has been achieved by non-covalent assembly of multilayer thin film supramolecular structures. The use of non-covalent assembly has been demonstrated for both systems which involve covalent interactions, for example peptides, and systems based on non-covalent interactions, for example, metal-ligand complexation. The non-covalent supramolecular thin film systems of the present invention substantially reduce the synthetic complications commonly encountered in the preparation of large covalent molecules and are capable of generating significant photocurrent.

The multilayered systems of the present invention are formed by a sequential deposition of alkanethiols terminated with 2,6-pyridinedicarboxylate ligands which complex with a variety of metal ions having different valences and capping groups with 2,6-pyridinedicarboxylate ligand termination at one end, for complexation with metal ions, and chromophore, photooxidant, photoreductant units or additional 2,6-pyridinedicarboxylate ligand termination groups for binding subsequent layers.

BRIEF DESCRIPTION OF THE DRAWINGS

This invention is pointed out with particularity in the appended claims. Other features and benefits of the invention can be more clearly understood with reference to the specification and the accompanying drawings in which:

DESCRIPTION OF THE PREFERRED EMBODIMENTS

Figure 1:
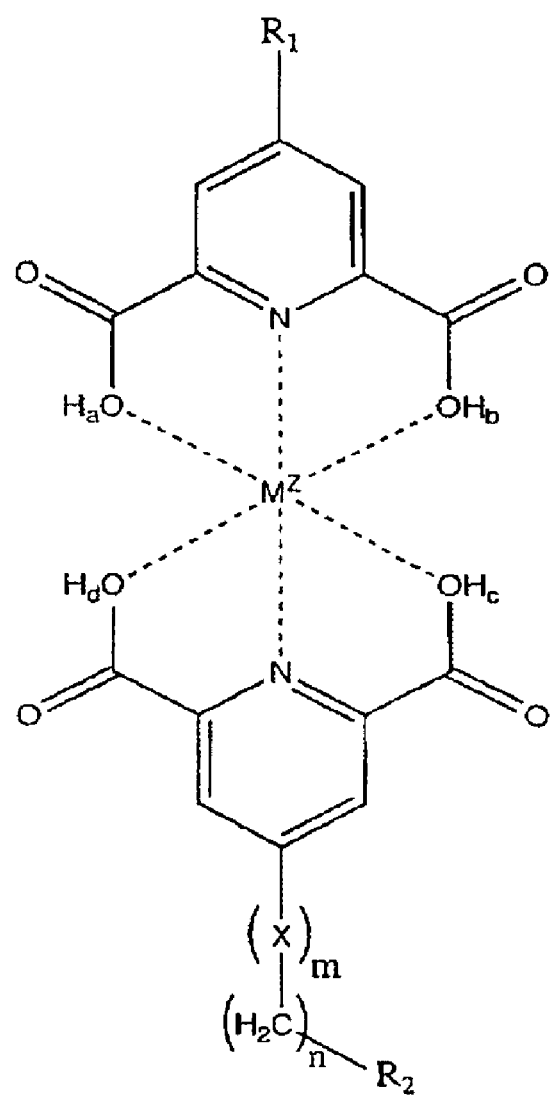
FIG. 1 shows a self-assembled monolayer chemical structure of the present invention.

A key advantage of the present invention over current state of the art for multilayer assembly is the advantageous features of the bis(2,6-pyridinedicarboxylate) metal linker used to join adjacent film layers in structures of the present invention. Current state of the art relies on strategies such as sequential deposition of Langmuir-Blodgett films or SAMs that rely on weak intermolecular interactions between molecules such as van der Waals (VDW) interactions and hydrogen bonding as well as metal-ligand coordination to control deposition and positioning of success layers of components. The inherently weak nature and reversibility of VDW and hydrogen bonding make them unsuitable for linkages with which to control multilayer assembly. Those few systems that utilize stronger metal-ligand interactions to link molecular components suffer from a very limited selection of organic ligands that generally are tailored to be compatible with a specific metal. Ligand systems that are compatible with several different metals have complex organic structures that are specialized and of limited utility as a generally compatible group for assembly of multilayers. Current state of the art systems cannot not yet offer a general linkage to control multilayer assembly that is robust, strong, directional, easy to incorporate and compatible across a wide range of organic components, functionality and metals.

The present invention provides advantages over the current state of the art that include the following: (1) metal-coordination by 2,6-pyridinedicarboxylate ligands provides a versatile bis(2,6-pyridinedicarboxylate) metal linkage that has a single predictable structure that persists across a range of metals and attached organic components; (2) the bis(2,6-pyridinedicarboxylate) metal complex provides a rigid linkage that aligns attached organic components in a linear arrangement that promotes assembly orthogonal to the surface; (3) the 2,6-pyridinedicarboxylate ligand is compatible with and can be covalently attached to a variety of organic components with a range of functional groups; (4) the bis(2,6-pyridinedicarboxylate) metal linkage is robust enough to fabricate multilayers via sequential deposition of different organic components that are incommensurate in size (i.e., components with different cross-sectional widths); (5) 2,6-pyridinedicarboxylate ligands form charge neutral bis(2,6-pyridinedicarboxylate) metal complexes by losing protons from the four carboxylic acid groups, which allows the complex to incorporate metals with 1+ to 4+ charge and remain neutral with no counterion that can affect structure and binding during multilayer assembly; (6) the bis(2,6-pyridinedicarboxylate) metal complexes accommodate a range of different metals without changing the molecular structure of the metal complex significantly, thus providing a unique means to control and systematically alter the electronic, magnetic and optical properties of the resultant multilayer films.

I. Components of SAMs and Multilayer Structures of the Present Invention

Figure 2:
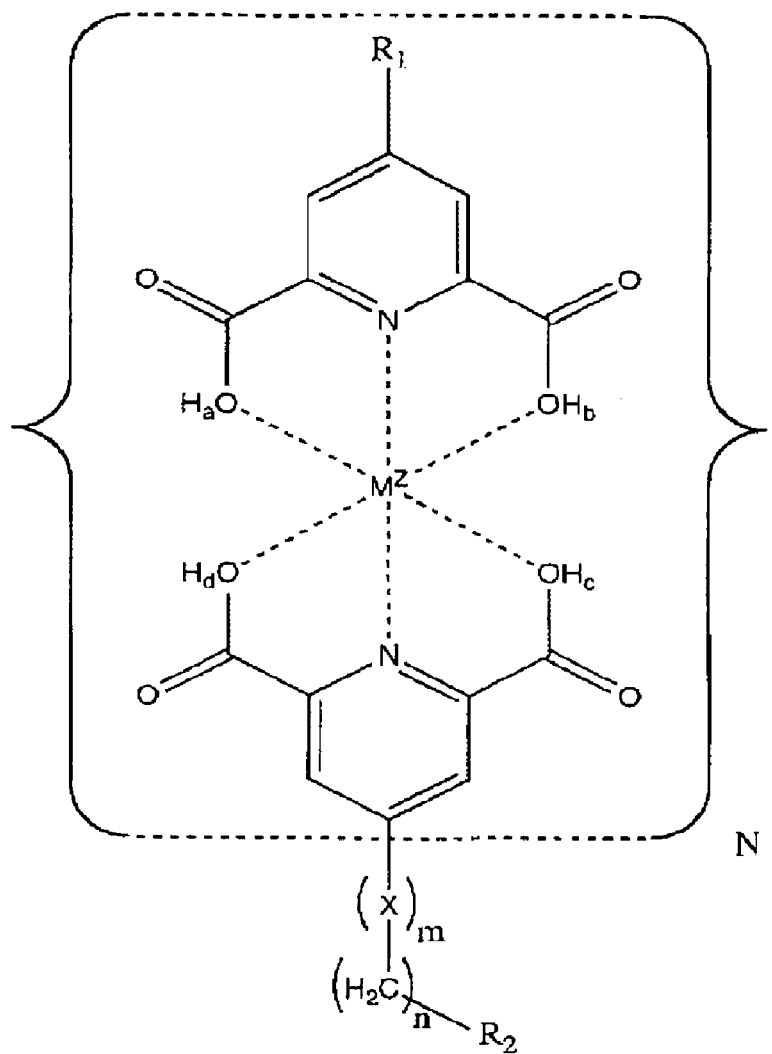
FIG. 2 shows multilayer thin film chemical structure of the present invention.

In refering to the typical SAM structure shown in FIG. 1 and multilayer structures shown in FIG. 2, the surface films of the present invention comprise a surface coupling agent, an alky chain linking the coupling group to a heteroatom which is employed for facilitating synthesis, metal ions and 2,6-pyridinedicarboxylic acid ("26PDA") ligands which complex with a variety metal ions to bind multilayered films and provide prefered ordinging and stability to the films.

A. 2,6-pyridinedicarboxylic Acid ("26PDA") Ligand

The 26PDA ligand forms bis(2,6-pyridinedicarboxylate) metal complexes that have a single persistent structure for a range of different transition metals. Two 26PDA molecules serve as tridentate ligands that bind transition metals in an octahedral geometry, regardless of the normally observed coordination geometries of the metals. For example, $Co^{+2}$, $Ni^{+2}$ and $Cu^{+2}$ normally coordinate ligands in octahedral, square planar and tetrahedral geometries, respectively. Coordination of these and other transition metals (e.g., $Mn^{+2}$ and $Zn^{+2}$) by 26PDA gives bis(2,6-pyridinedicarboxylate) metal complexes in which all of the metals are coordinated octahedrally. An example of this octahedral coordination as shown for $Cu^{+2}$. This coordination behavior shows that 26PDA generally dictates the coordination geometry rather than the metal. Note: exceptions to this mode of coordination are $Pd^{+2}$ and $Pt^{+2}$, which form square planar complexes involving the pyridine nitrogen and only one of the carboxylic acid groups on each 26PDA ligand.

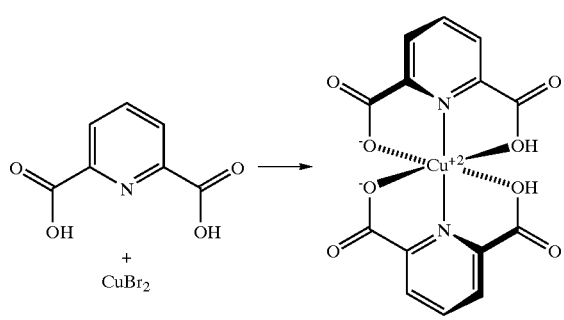

Octahedral coordination in bis(2,6-pyridinedicarboxylate) metal complexes forms rigid structures that align para substituents, R, in a linear arrangement on opposite ends of the complex. Thus, the bis(2,6-pyridinedicarboxylate) metal complex serves as a building block that can be used to assemble and align two organic groups (R) in a linear arrangement. In the context of SAMs, this means that sequential assembly of SAMs by alternating deposition of organic layers and metal layers can be controlled to occur orthogonal to the surface. The structure at the junction between organic layers is defined by the rigid bis(2,6-pyridinedicarboxylate) metal complexes that link and align the organics on either side.

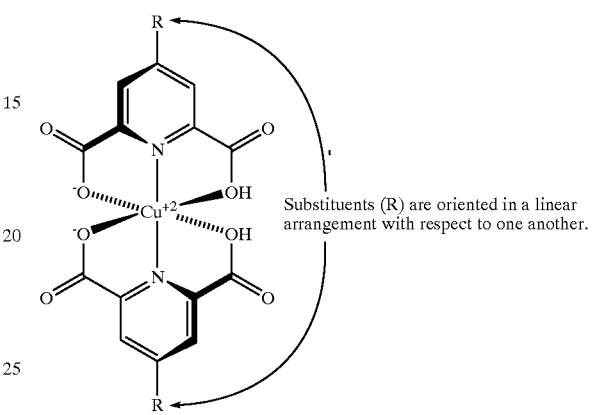

Substituents (R) are oriented in a linear arrangement with respect to one another.

The bis(2,6-pyridinedicarboxylate) metal complexes can accommodate a range of different transition metals without changing the molecular structure of the metal complex significantly. This means that the properties of the complexes and multilayer films based on these complexes can be controlled and altered by changing the metal. The organic 26PDA ligands define a single mode of binding and a consistent molecular structure, while the metal is an interchangeable component. This feature is convenient from a structural viewpoint in that a variety of different metals can be used without changing the structure of the metal complex. The structure is constant with regard to the metal complex at the juncture between organic layers in multilayer films. Importantly, the interchangeability provides a convenient way to vary the electronic properties of multilayer films. For example, we have shown photogenerating multilayer films can be constructed with Cu, Co and Zn. Although the multilayer films are similar in structure and structural properties, the electronic potential at which they switch from cathodic to anodic behavior differs depending on the metal that is present. These results indicate clearly that the metal plays an electronic role as well as a structural role.

Different metal complexes can be mixed together to form solutions or segregated into different areas of a material. The crystal work shows that mixing two or more different metal complexes in the same solution results in mixed crystals that contain solid solutions of the different metal complexes randomly distributed throughout the crystal. The crystal work also shows that one metal complex can be deposited/grown on the surface of a substrate crystal of a different metal complex to produce composite crystals that contain different metal complexes segregated in different regions of the crystal. Mixing and epitaxial deposition of the different metal complexes is possible because the structure of the complex is consistent across a series of different metals. Similarly, it should be possible to use combinations of different metals during the assembly of multilayer films. For example, exposing a SAM with 26PDA head groups to a solution with two or more different types of transition metals, followed by exposure to another organic with 26PDA head groups will give a multilayer film with a mixed layer of metals. Exposing a SAM with 26PDA head groups to one type of metal, followed by an organic with 26PDA head groups at both ends, followed by deposition of a second type of metal and then another organic with 26PDA head groups will give a multilayer with different metals segregated in different layers. This type of system is useful, for example, in the design of photogenerating multilayer films in which the layers of different metals create a downhill gradient of electrochemical potential that helps shuttle electrons away from a layer of photoactive chromaphores in order to minimize charge recombination. Although groups such as Thompson's have utilized different metals in different layers as a method to construct multilayer films, they were not able to characterize structure at the interface between organic and metal layers. The structure of the bis(2,6-pyridinedicarboxylate) metal complex is known and thus predictable across a range metals.

Bis(2,6-pyridinedicarboxylate) metal complexes can accommodate metals that vary in charge from 1+ to 4+. 26PDA ligands form charge neutral bis(2,6-pyridinedicarboxylate) metal complexes by losing protons from the carboxylic acid groups. This unique property allows the complex to incorporate metals with 1+ to 4+ charge and remain neutral with no counterion to balance charge. This feature is ideal for multilayer assembly since counterions affect both the structure and properties of SAMs and multilayer films.

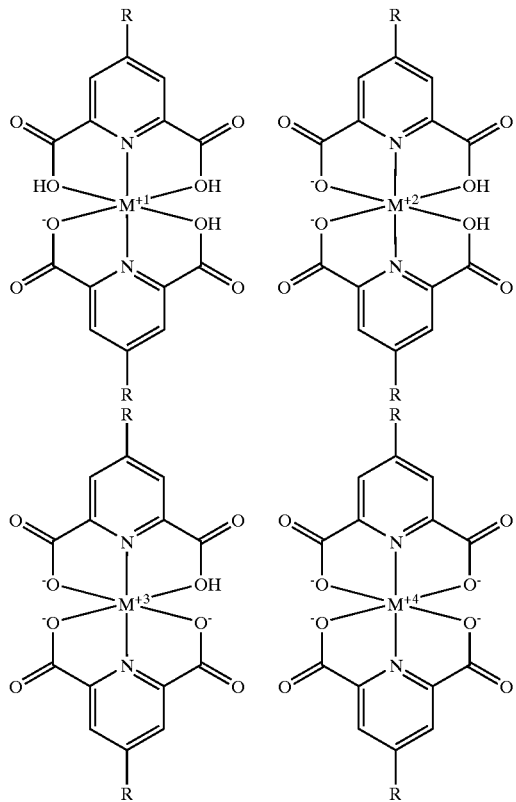

26PDA ligands can be used to assemble layers of different organic components that are incommensurate in size. A SAM of alkane thiol with 26PDA headgroups forms a well-ordered layer in which the packing density is defined by the cross-sectional area of the terminal 26PDA groups exposed on the surface. Subsequent addition of organics larger than 26PDA results in a second layer with lower packing density that prevents one-to-one binding between the 26PDA groups at the interface. We have demonstrated that fabrication of well-ordered multilayer films can be achieved easily using metal complexation between 26PDA ligands despite incommensurate binding that results from mismatches in the size of components. For example, we have shown that pyrene substituted with a 26PDA ligand forms a well-ordered multilayer film on a SAM of 26PDA-terminated alkane thiol on gold despite that fact that the pyrene units are considerably larger than the underlying 26PDA units. The fact that this multilayer film forms an nonconductive insulating surface shows that the pyrene layer is highly ordered dispite incommensurate binding.

26PDA ligands form tris(2,6-pyridinedicarboxylate) lanthanide metal complexes that have a single persistent structure for a range of different transition metals. We have studied the crystal structures of all but two of the lanthanide metal complexes with 26PDA and imidazole. This work is unpublished. These complexes position substituents, R, in a trigonal planar arrangement around the periphery of the complex. Consequently, they are not useful for linear assembly orthogonal to surfaces in the same way that transition metal complexes are. These complexes at least demonstrate the utility of the 26PDA ligand for binding metals other than transition metals that are much larger. The lanthanide metal complexes behave similar to those of the transition metal series in our 2000 JACS paper in that the series is isostructural in terms of molecular structure and crystal structure. They form mixed and composite crystals similar to those formed with transition metals.

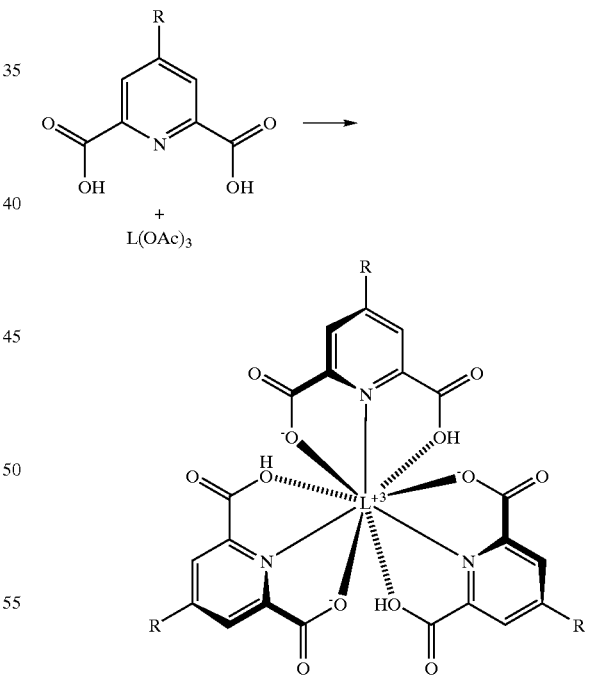

B. SAMs Coupled to 2,6-pyridinedicarboxylic Acid ("26PDA") Ligands

FIG. 1 shows the generic structure of a SAM of the present invention. This structure forms the basis for multilayered structures shown in FIG. 2 where either bonding on metal surfaces such as gold, copper, platinum and can be readily achieved through the use of a surface coupling group, such as sulfur or silicon, which form either metal-sulfur bonds or silicon-oxygen bonds for subtrates such as silicon oxide and Indium tin oxide. For silicon bonds, a silicon compound, for example tricholorosilyl is typically employed. In FIG. 1, m=0 or 1 and X is a non-carbon heterotaom such as oxygen, sulfur or nitrogen, which is provided for synthetic utility since it is easier to couple alkyl chains to pyridine through a heteroatom. Here $M^z$ represents a postiively charged metal ions including but not limited to Cu(II), Co(II), Fe(III), Fe(II), Zn(II), Mn(II), transition metals and lanthanide metals where z=+1 to +4. In preferred embodiments, ions which complex with 26PDA ligands and form complexes with neutral charge are employed. In this structure, the —OH groups either lose hydrogen or retain hydrogen and in maintaining a neutral charge balance when forming ligand complexes with various ions having a varying valances. Thus a, b, c and d equal 0 for no hydrogen or 1 for retained hydrogen and the total number of retained hydrogens a+b+c+d+=4−z to maintain charge neutrality. Alkyl chains are typically employed to link the surface coupling agent to the substrate where the number of cargons range from n=0 to 20 or larger depending on the stability of the film on the surface.

C. Multilayered Thin Film Structures

FIG. 2 shows the generic structur of multilayered thin film supramolecular sturctures of the present invention. This structure comprises the SAM of FIG. 1 and aditional repeating units of the 26PDA-metal ligand structure for binding additional layers. Typically N is greater than one for mulitlayered films. Examples of multilayered fims are provided in FIGS. A–3D and FIGS. 4A–4C and discussed below.

D. Connector Ligands

In some preferred embodiments, a connector ligand is sandwiched between successive layers of metals complexes. In one prefered embodiment, 2,2',6,6'-tetracarboxy-4,4'-bypyridyl is employed as a connector ligand. In alternative embodiments 2,2',6,6'-tetracarboxy-4,3'-bypyridyl is employed as a connector ligand. In other preferred embodiments, chromophors, or photoxidant or photorecuctant groups may be employed as either electron donors or electron acceptors.

E. Linking Structures

Figure 7A:
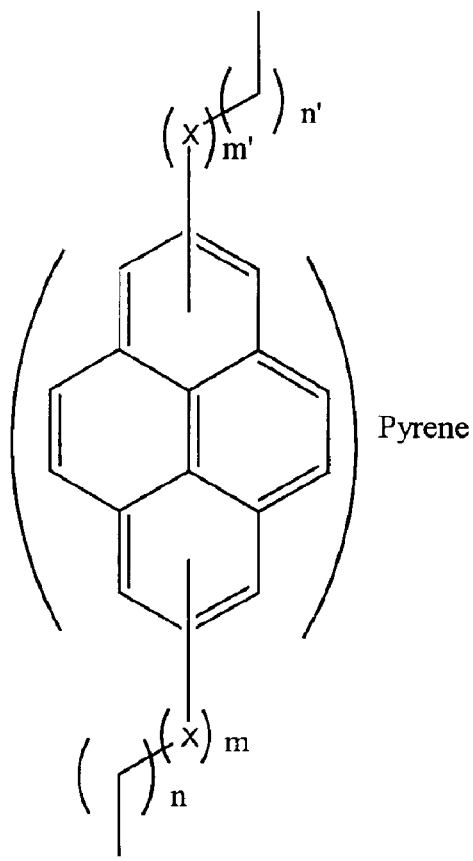
FIGS. 7A–7B show example linking groups comprising Pyrene (FIG. 7A) and Porphyrin (FIG. 7B)
Figure 7B:
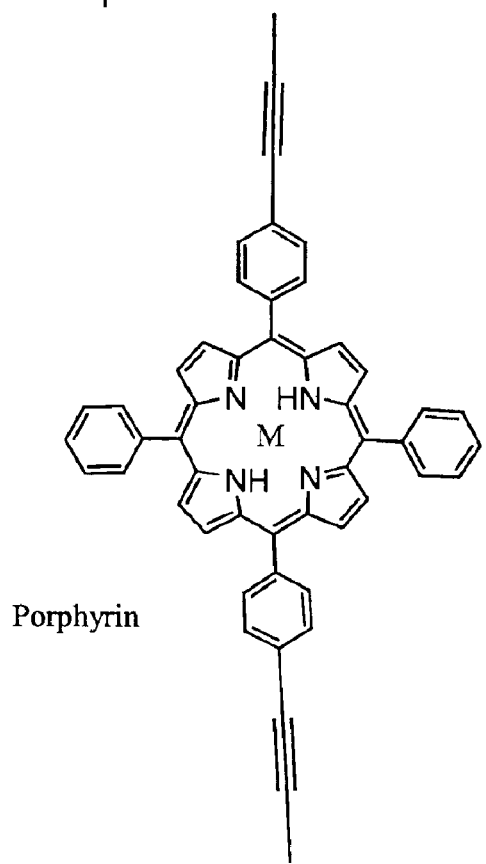

FIG. 7A shows a typical linking structure comprising a pyrene group shown as one example. In some preferred embodiments, the linking structure comprises is a light absorbing group or photooxidant or photoreductant which is substituted with linking type structures that serve to connect L to the pyridine groups. Here n=0 to 20 with the number defined by the efficiency of the constructed films. Here n' is the same as n unless L is the top-most layer in which case n=0. Here X is a heteroatom or some other more complex linking group which could be an alkene or multiple alkenes or an alkyne or multiple alkynes (shown below as an example). X' is the same as X or different or is nothing when this L is in the top most layer of the film. FIG. 7B shows another embodiment of a linking structure comprising tetraphenyl porphyrin where X is an alkyne, for example acetylene and ne=0 and M is a metal typically found in porphyrin structures, for example Zn.

F. Ligand Termination Groups

Figures 3A, 3B, 3C, 3D:
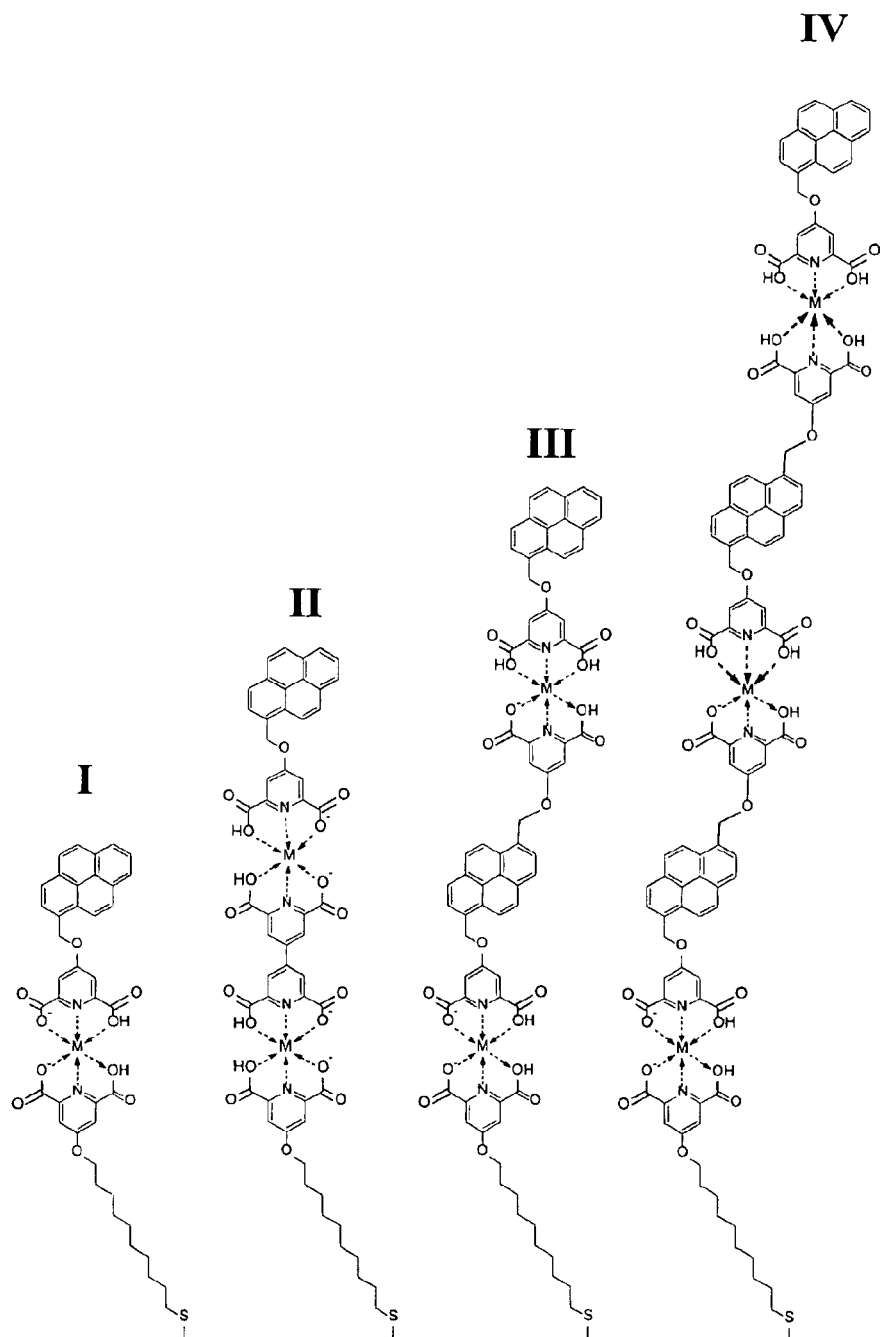
FIGS. 3A–3D show various multilayer chemical structure embodiments of the present invention having increasing complexity.
Figures 4A, 4B, 4C:
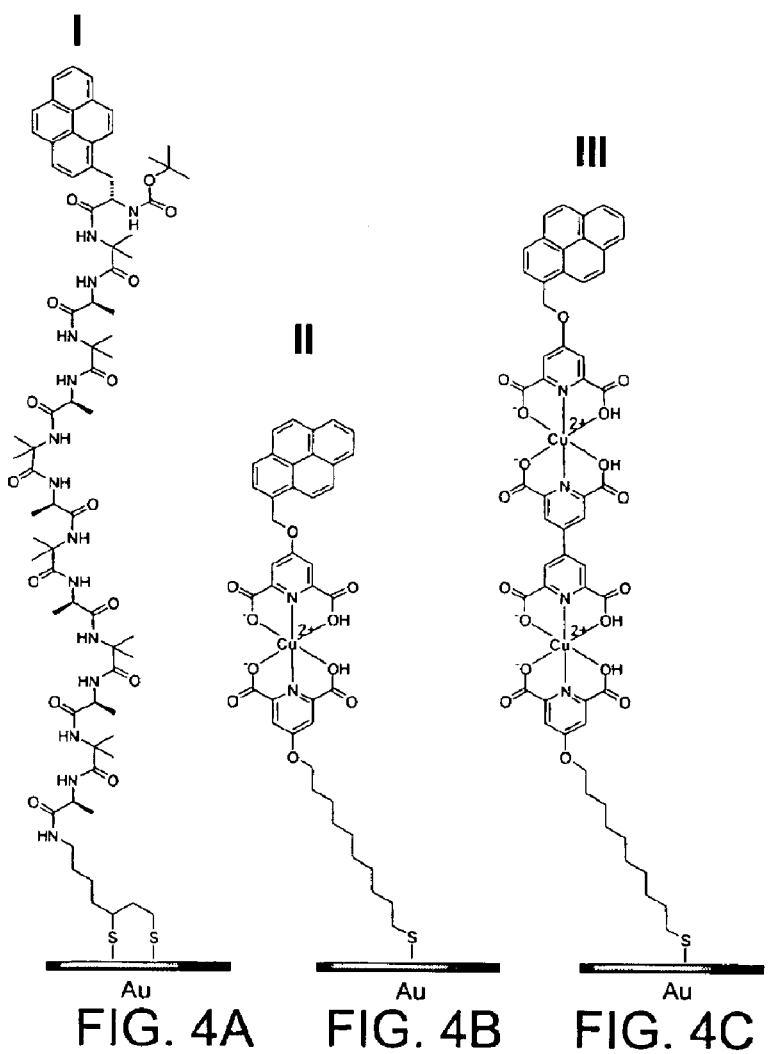
FIGS. 4A–4C shows embodiments of a SAM baseline structure (FIG. 4A) and multilayer films of increasing complexity (FIGS. 4B–4C) of the present invention.

As shown in FIGS. 3A–3D and FIGS. 4A–4C, ligand termination groups are typically employed that comprise the complexing ligand (the 2,6-dicarboxypyridine with substitution at the 3, 4, or 5-positions together with a light absorbing (chromophores) or electron accepting or donating groups the choice of which would depend on the underlying layers, i.e., whether said layers contain chromophores or electron donating/accepting groups. In preferred embodiments, chromophores such as pyridine, pyrene, perylene, naphthaline, anthracien, or other fused aromatics, porphyrins, mono-, di-, tri-, tetraphenyl porphyrins, bensoporphhyrins, mono-, di-, tri-, tetraphenylbenzoporphyrins or phtalocyanines may be employed or chromophores with appropriate photooxidation/phototreduction behavior. Alternatively, these could be porphyrins with various substitutions, for example substituting tetraphenyl porphyrins at alternate phenyl groups with dicarboxypyridines where the pyridines are attached directly to the phenyl groups at the 4-position or where the pyridines are attached to the phenyl groups by way of an acetylene group. In other embodiments, photooxidizing compounds such as methyl viologen, substituted methylviologens, quinoes, substituted quinoes and molecules having small negative reduction potentials as determined form the Gibbvs free energy change determined from the Rohm-Weller equation may be employed. Alternatively, photoreducing compounds such as EDTA or other tertiary and secondary amines, aromatics containing alkocy groups or other molecules havimg small positive oxidation potentials per the Rohm-Weller equation. The idea in either case is to have a rigid link between the porphyrins and the pyridines so that the porphyrins will stick up from the surface. We have observed that without a rigid link, the porphyrins tend to lie down on the surface and prevent any further layers from assembling II. Synthesis and Characterization of Simple Film Structures Initially, three types of photocurrent generating thin films on a gold surface were fabricated as shown in FIGS. 4AB–4C. SAM I (FIG. 4A) consists of a pyrene chromophore coupled to a helical peptide that is attached to a gold surface through an alkyldisulfide linker and is similar to systems reported previously by Kimura et al. which exhibit photocurrent generation. SAM I served as a baseline benchmark for comparision with films II (FIG. 4B) and III (FIG. 4C) of the present invention which are multilayered systems in which the light absorbing group (e.g. pyrene) is non-covalently coupled to a gold surface via metal-ligand complexation. These systems are non-covalently assembled by sequential deposition of three or more components. In film II, three components are used: decanethiol linked to a 4-pyridyl-2,6-dicarboxylic acid ligand; Cu(II) ions; and a pyridyl-2,6-dicarboxylic acid ligand linked at the 4-position through a methylenyloxy group to the 1-pyrenyl chromophore. Film III possesses two additional non-covalently linked layers: a 4,4'-bipyridyl-2,2'6,6'-tetracarboxylic acid was deposited after Cu(II) followed by another layer of the same metal ion and finally the pyrene-containing ligand. Details of the synthesis of SAM I, and films II and III and the method of deposition are provided below.

Most reagents and solvents used in the synthesis of films I, II, and III were obtained from Aldrich and were used as received. Amino acids with the appropriate protecting groups were purchased from Advanced Chemtech. Chelidamic acid was purchased from Fluka. In experiments using acetone, the solvent was dried over anhydrous sodium sulfate and distilled immediately before the experiment. NMR spectra were obtained in an Avance Bruker spectrometer at 400 MHz for proton and 85 MHz for $^{13}$C. All NMR spectra were obtained in deuterochloroform solutions, unless otherwise indicated. Mass spectra were obtained with an LC-MS using the electrospray ionization technique.

A. Synthesis of Film I (FIG. 4A)

(i) 1-(Bromomethyl)pyrene 2 g (8.62 mmol) of 1-pyrenylmethanol was dissolved in 60 mL of benzene at 40° C. To this solution 0.4 mL of phosphorous tribromide was added dropwise and the solution was refluxed for 4 hours. The mixture was cooled and partitioned in a mixture of ether/water 3:2. The organic extractions were triple rinsed with water and dried over anhydrous sodium sulfate. The ether was evaporated and 2.43 g of a yellow powder was obtained. Yield: 96%. $R_f$=0.83 ($CH_2Cl_2$ as mobile phase), 0.95 (hexane/ethyl acetate 1:1 as mobile phase); m.p.: decomposes above 270° C.; $^1$H-NMR: 5.26 (s, 2H, $CH_2$); 7.98–8.85 (m, 9H, pyrene); $^{13}$C-NMR: 32.65 ($CH_2$); 123.2–132.3 (aromatic C, pyrene).

(ii) Diethyl 2-(1-pyrenylmethyl)-2-acetamidomalonate. 1.74 g (8.0 mmol) of diethylacetamidomalonate and 0.24 g (10 mmol) of NaH were placed in a two necked flask under nitrogen. The flask was placed in an ice bath and THF was added dropwise under nitrogen and with stirring. The solution was allowed to stand for 5 minutes and then 0.5 mL of anhydrous ethanol was added. The solution was warmed to room temperature. In a separate flask, under nitrogen, 2.3 g (8.0 mmol) of 1-(bromomethyl)pyrene was dissolved in THF. Both solutions were combined and stirred at room temperature for 15 minutes and then refluxed for 18 hours. After reflux, the solvent was removed under reduced pressure and the product was partitioned between dichloromethane and water in a separatory funnel. The organic fraction was washed with water, dried over anhydrous sodium sulfate and the solvent was removed. The reaction was followed by TLC using ethanol/water (4:1) as the mobile phase. Yield: 83%. $^1$H-NMR: 1.42 (t, 6H, $CH_3$); 1.95 (s, 3H, $COCH_3$); 3.75 (d, 2H, Py-$CH_2$); 4.35 (m, 4H, $CH_2$); 6.42 (s, 1H, NH); 7.7–8.2 (m, 9H, pyrene); $^{13}$C-NMR: 12.1; 21.2; 23.7; 32.7; 51.6; 121–129 (pyrene); 165.8, 167.8 (C=O)

(iii) N-Acetyl-DL-1-pyrenylalanine. 2.5 g (7.5 mmol) of diethyl 2-(1-pyrenylmethyl)-2-acetamidomalonate was dissolved in a mixture of 80% ethanol and 20% water. 1.27 g (22.6 mmol) of KOH was added. The solution was refluxed for 18 hours. The pH of the solution was adjusted to 2.0 with hydrochloric acid and refluxed for a further two hours. The solution was adjusted to pH 10, transferred to a separatory funnel and washed with dichloromethane to remove organic impurities. The aqueous layer was acidified again to pH 2.0 and then extracted with dichloromethane. The solvent was removed under reduced pressure. The reaction was followed by reverse phase TLC using ethanol/water (4:1) as mobile phase. Yield: 98%. $R_f$=0.45 (dichloromethane/methanol/acetic acid 8:1:0.5 as mobile phase); m.p.: 215–218° C.; MS: $(M+H)^+$ at 332.2 (calc. 332.1)

(iv) L-1-pyrenylalanine. 2 g (6.9 mmol) of N-Acetyl-DL-1-pyrenylalanine was suspended in water and the pH adjusted to 8.0 with 2N NaOH. A catalytic amount of cobalt chloride hexahydrate (less than 1 mg per mmol amino acid) with aminoacylase, from *Aspergillus* Acylase, (52 mg per mmol amino acid) was dissolved in water, filtered to remove insoluble materials and added to the pyrenylalanine solution. The solution was placed in an orbital shaker at 37° C., 200 rpm for 2 days. The resulting precipitate was separated by centrifugation, washed with water and dried by lyophilization to give an off-white solid. Yield: 48%. $R_f$=0.73 (dichloromethane/methanol/acetic acid 8:1:0.5 as mobile phase); m.p.: 205–210° C.; MS: $(M+H)^+$ at 290.2 (calc. 290.1)

(v) N-t-butoxycarbonyl-L-1-pyrenyl alanine (tBoc-PyAla). 1 g of L-1-pyrenyl-alanine was suspended in 100 mL of a water/dioxane (1:1) mixture. A solution of 1 g of di-tert-butyloxycarbonyl ($Boc_2O$) and 0.5 g of triethylamine in 20 mL of water/dioxane (1:1) was added to the L-1-pyrenylalanine suspension, under stirring at 0° C. The solution was stirred at 0° C. for 3 hours and then at room temperature for 24 hours. The reaction was followed with TLC using $CHCl_3$/MeOH/AcOH (90:10:3) as the mobile phase. The solution was filtered to recover the unreacted L-1-pyrenylalanine (36%) and the solvent was removed. To the remaining brown oily residue, a small amount of water was added (5 ml) and then the solution was acidified to pH 4 with 5% citric acid. The acidified solution was extracted with ethyl acetate. The organic extractions were washed with water and dried with anhydrous sodium sulfate. The solvent was removed and ether was added to the remaining oil until precipitation of the product occurred. The final product was filtered and dried under vacuum and then recrystallized with chloroform/ether. A white powder was obtained. Yield: 20%. $R_f$=0.45 (chloroform/methanol/acetic acid 90:10:3 as mobile phase); $^1$H-NMR (DMSO): δ(ppm) 1.49 (s, 9H, $CH_3$); 3.29, 3.60 (m, 2H, $CH_2$); 4.41 (d, 1H, CH); 7.47 (d, 1H, NH); 7.73–8.53 (m, 9H, CH pyrene); $^{13}$C-NMR (DMSO): δ(ppm) 22.2 ($CH_3$ from t-Boc); 34.5 ($CH_2$); 53.5 (CH); 122.9–132.0 (pyrene); 169.1, 173.1 (C=O); MS ($M^+$) at 389.2 (calc. 389.4)

(vi) Peptide (Aib-Ala)$_6$. The backbone peptide (Aib-Ala)$_6$ was synthesized using a solid phase method starting with a FmocAla-Wang resin. FmocAla-OH and FmocAibOH were double-coupled from DMF solutions containing 2.5 eq. of the peptide, 2.5 eq HOBt, 2.5 eq PyBop and 5 eq. DIPEA. The reaction time for each coupling was approximately 3–6 hours with shorter coupling times used with alanine residues and longer times for aib residues. Fmoc-deprotection was carried out with 20% piperidine in DMF. All reactions were run under nitrogen. When the total sequence was completed, the last amino acid was deprotected and the resin was washed 3 times each with DMF, $CH_2Cl_2$, ethanol and methanol. The resin was dried under vacuum for 3 hours. Then, a solution of 95% TFA, 2.5% water and 2.5% triisopropyl silane was used to cleave the peptide from the resin. The resin was filtered out of the solution. TFA and the scavengers were removed by rotary evaporation. Ether was added to the remaining residue and the solution was stored at 0° C. until precipitation of the peptide occurred. The final product was filtered and dried under vacuum. The peptide purity was confirmed with HPLC using acetonitrile/water 50:50 as mobile phase. Yield: 79%. $^1$H-NMR: δ(ppm) 1.23 (d, 18H, $CH_3$ Ala); 1.76 (s, 36H, $CH_3$ Aib); 3.50 (m, 6H, CH Ala); 7.47–8.87 (m, NH); MS: $(M+H)^+$ at 955.8 (calc. 956.0); $(M+Na)^+$ at 977.6 (calc. 978.0).

(vii) 1,2-dithia-3-(1-amino-n-pentyl)cyclopentane (lipoamine or LA)$^8$. 1 g of dl-□-lipoamide was dissolved in 100 mL THF. The solution was added to a dispersion of 0.826 g of $LiAlH_4$ in 50 mL THF. The mixture was refluxed for 15 hours. After that it was cooled to 0° C. and 10 mL of distilled water were added and the solution was stirred for 30 minutes. The solvent was removed and methanol was added to the residue. The solution was filtered and methanol was removed. To the residue from the methanol phase, 100 mL of water was added and the pH was adjusted to 6.5 with 1 N HCl. The solution was stirred at room temperature for 1 day. The final product was extracted with n-butanol. The organic extractions were washed twice with 1 N NaOH and 1 N HCl. The solvent was removed to afford a yellow powder The reaction was followed by TLC using dichloromethane:methanol:acetic acid (90:10:3) as the mobile phase. Yield: 25%. $R_f$=0.18–0.20; $^1$H-NMR: δ(ppm) 1.48 (m,4H,$H_2$N—$CH_2CH_2CH_2CH_2CH_2$), 1.71 (m, 4H, $H_2$N—$CH_2CH_2CH_2CH_2CH_2$), 1.89, 2.28 (m, 2H, $CHCH_2CH_2$SS); 2.40 (m. 2H, $H_2NCH_2$); 3.15 (2H, m, $CHCH_2CH_2$SS); 3.59

(m, 1H, CHCH$_2$CH$_2$SS); $^{13}$C-NMR: 26.4, 27.4, 28.7, 34.6, 38.5, 40.3, 42.8 (7-CH$_2$); 56.8 (CH).

(viii) Coupling of LA to the Peptide C-terminus: (Aib-Ala)$_6$-LA$^8$. The peptide was dissolved in DMF and was added dropwise to a solution of 5 equivalents each of LA, HATU and DIPEA at 0° C. The high ratio of coupling reagents and the slow addition of the peptide helps to decrease the rate of possible alternate reactions. The solution was stirred at 0° C. for 30 minutes and then at room temperature for 24 hours. DMF was removed and the residue was dissolved in chloroform. The solution was washed with 4% aqueous sodium bicarbonate and 4% sodium bisulfate. The organic fractions were dried over sodium sulfate, chloroform was removed and the residue was purified with column chromatography using methanol as the eluent. The final product was further recrystallized from chloroform/hexane. Yield: 25%. $^1$H-NMR: δ(ppm) 1.26–1.71 (m, 63H, CH$_3$ from Aib and Ala+9H from lipoamine fragment), 2.5–3.7 (m, 6H from lipoamine+6 CH from Ala); 7.5–8.5 (12 NH); MS: (M+Na)$^+$ at 1151.6 (calc.1151.3)

(ix) Coupling of tBocPyAla to (Aib-Ala)$_6$-LA: tBocPyAla-(Aib-Ala)$_6$-LA (I)$^8$. 1 mmol of the N-free side peptide was dissolved in DMF. The solution was cooled down to 0° C. and a solution of 2.5 equivalents of Boc-pyrenyl-alanine, 2.5 eq of HATU and 2.5 of diisopropyl-ethylamine (DIPEA) were added. The solution was stirred at 0° C. for 30 minutes and then at room temperature for over 24 hours. The reaction was followed with TLC using chloroform/methanol/ammonium hydroxide (13:5:1) as the mobile phase. After the reaction was completed, the solvent was removed under reduced pressure and the residue was dissolved in chloroform. The insoluble residue was separated by filtration. The chloroform solution was washed twice with 4% sodium bicarbonate solution and 4% sodium bisulfate solution. Finally the organic phase was dried over anhydrous sodium sulfate and the solvent removed under reduced pressure. A white-brown powder was obtained and recrystallized from chloroform/ether. Yield: 80%. The final product has an R$_f$=0.40 chloroform/methanol/ammonium hydroxide (13:5:1) as mobile phase; $^1$H-NMR: δ(ppm) 1.35–2.0 (broad band, 71H, 54H from CH$_3$ from Ala and Aib units, 9 from CH$_3$ tBoc, 2H from lipoamine ring CH$_2$CH$_2$CHSS and 8 CH$_2$ from lipoamine chain); 3.15–3.20 (m, 6H, 2 from CH$_2$ lipoamine ring, CH$_2$NH lipoamine chain and CH$_2$ PyAla); 3.53 (m, 1H, CH lipoamine ring); 3.95–4.24 (m, 6H, CH Ala); 4.41 (CH PyAla); 7.30–8.12 (22H, 9 aromatic H from Py+12 NH); $^{13}$C-NMR: δ 14.2, 22.7, 23.3 (CH$_3$ from tBoc, Aib and Ala respectively); 26.5, 29.4, 30.1, 32.0, 35.1, 38.8, 38.9, 40.2 (CH$_2$ from lipoamine and from PyAla at 32.0 and 35.1); 56.4 (CH from lipoamine ring); 53.5 (CH from PyAla); 50.6 (CH from Ala); 123.1–131.3 (Aromatic C); 169.7–171.2 (carbonyl carbons)

B. Synthesis of the Molecular Components Contained in Films II (FIG. 4B) and III (FIG. 4C).

1. 4-(10-sulfhydryl-decyloxy)-pyridine-2,6-dicarboxylic Acid.

(i) Diethyl 4-hydroxypyridine-2,6-dicarboxylate$^{4,20,21}$. 6.2 mL of thionyl chloride (85 mmol) was added dropwise to 25 mL of ice-cold ethanol. To this solution 2.5 g (13.7 mmol) of chelidamic acid was added. The solution was stirred at room temperature for 20 h and then refluxed for 2 hours. The solution was then cooled in an ice bath and the solvent was removed by rotary evaporation. 20 mL of water was added to the residue and the mixture was cooled to 0° C. After cooling, the mixture was neutralized with 5 mL of 10% aqueous sodium carbonate and 5 mL of ethanol-water (1:2). The solution was filtered and the white product was dried under vacuum to afford 3.26 g. The reaction was followed by TLC using methanol as mobile phase. Yield: 99%. R$_f$=0.65 (methanol as mobile phase). m.p.: 115–116° C. (124–125° C.$^{19}$; 120–121° C.$^{17}$); $^1$H-NMR: δ(ppm) 1.45 (t, 6H, CH$_3$); 4.46 (q, 4H, CH$_2$); 7.31 (m, 2H, aromatic); 9.96 (bs, 1H, OH); $^{13}$C-NMR: 14.5 (CH$_3$); 63.9 (CH$_2$); 120.8 (Ar—C); MS: (M+Na)$^+$ at 262.3 (calc. 262.2)

(ii) 4-(10-Bromodecyloxy)-pyridine-2,6-dicarboxylate$^{22}$. 2 g (8.4 mmol) of diethyl 4-hydroxypyridine-2,6-dicarboxylate and 7.6 g (25.2 mmol) of 1,10-dibromodecane were dissolved in 100 mL of dry acetone. 2.32 g (16.8 mmol) of potassium carbonate was added. The solution was heated to reflux for 40 h and the reaction was monitored with TLC using chloroform-hexane (1:1). After the reaction was completed, the solvent was removed and the residue was dissolved in dichloromethane. The solution was filtered and the solvent was evaporated. The residue was purified with column chromatography. The final product was eluted with dichloromethane-hexane (1:1) as mobile phase. Yield: 75%. $^1$H-NMR δ(ppm) 1.24–1.48 (m, 20H, 14 from CH$_2$ and 6 from CH$_3$); 1.86 (m, 2H, CH$_2$CH$_2$—Br); 3.41 (t, 2H, CH$_2$—Br); 4.13 (t, 2H, O—CH$_2$—(CH$_2$)$_9$); 4.48 (t, 4H, O—CH$_2$CH$_3$); 7.74 (s, 2H, pyridine); $^{13}$C-NMR=14.6 (CH$_3$); 26.2, 28.5, 29.1, 29.6, 29.7, 29.8, 33.2, 34.5 (CH$_2$); 60.8, 69.4 (O—CH$_2$); 114.7, 150.5, 165.2 (pyridine ring); 167.4 (C=O).

(iii) 4-(10-Thioacetyl-decyloxy)-pyridine-2,6-dicarboxylate$^{22}$. 1.20 g (2.6 mmol) of 4-(10-bromodecyloxy)-pyridine-2,6-dicarboxylate and 0.35 g (3.36 mmol) of potassium thioacetate were dissolved in 100 mL ethanol and the solution refluxed for 24 h. The resulting white precipitate was filtered and dried under vacuum. The product was used in subsequent steps without further purification or characterization, due to its low solubility in most organic solvents.

(iv) 4-(10-Sulfhydryl-decyloxy)-pyridine-2,6-dicarboxylic acid$^{22}$. 1.13 g of the product obtained in the previous step was suspended in 75 mL ethanol. A 0.2 N KOH solution in ethanol was prepared. The KOH solution was added dropwise, at room temperature and with stirring. The solution was stirred for 15 minutes and the reaction was quenched by adding 10 drops of acetic acid. The solvent was removed and the residue was dissolved in dichloromethane. The organic solution was washed with water and dried with anhydrous sodium sulfate. After dichloromethane was removed, a colorless compound was obtained. $^1$H-NMR δ(ppm) 1.24–1.44 (m, 16H, CH$_2$); 1.85 (s, br, 1H, SH); 2.51 (m, 2H, CH$_2$—S); 4.23 (br, 2H, O—CH$_2$); 6.49 (s, br, 2H, COOH); 7.88 (s, 2H, pyridine); MS=(M+H)$^+$ at 356.2 (calc. 356.4)

2. 4-(Methylpyrenyl)oxypyridine-2,6-dicarboxylic Acid$^{22}$.

(i) Diethyl 4-(methylpyrenyl)oxypyridine-2,6-dicarboxylate. 0.9 g (3.75 mmol) of 1-bromomethylpyrene and 1 g (3.40 mmol) of diethyl 4-hydroxypyridine-2,6-dicarboxylate were separately dissolved in acetone. The clear solutions were mixed and 0.37 g (3.5 mmol) of sodium carbonate were added. The solution was filtered and the solvent was removed to afford a yellow product. After drying under vacuum the product was recrystallized from dichloromethane to yield 1.17 g. Yield: 77%. R$_f$=0.40 (dichloromethane/methanol 1:1 as mobile phase); m.p.: 154–156° C. $^1$H-NMR: 1.46 (t,6H,CH$_3$); 4.47 (q,4H, CH$_2$); 5.90 (s, 2H, CH$_2$); 8.01–8.26 (m, 11H, aromatic H); $^{13}$C-NMR: 15.2 (CH$_3$); 30.2 (CH$_2$); 63.5 (CH$_2$); 115.7–131.6

(aromatic CH); 165.7, 169.0 (C=O). MS: (M+Na)⁺ at 476.8 (calc. at 476.5)

(ii) 4-(Methylpyrenyl)oxypyridine-2,6-dicarboxylic acid. 1.15 g (2.5 mmol) of diethyl 4-(methylpyrenyl)oxypyridine-2,6-dicarboxylate was dissolved in 60 mL ethanol. 9 mmol of potassium hydroxide was added and the solution was refluxed for 6 hours. The solution was diluted with water and acidified to pH 2.5 with 6 N HCl. A white product was precipitated at low pH and the solution was filtered. The product was washed with water, methanol and dichloromethane and dried under vacuum. 0.98 g was obtained. Yield: 97%. $R_f$=0.46 (dichloromethane/methanol 1:1 as mobile phase); m.p.: decomposes above 225° C. ¹H-NMR (DMSO): δ(ppm) 6.10 (s, 2H, $CH_2$); 7.92–8.41 (m, 11H, Ar—H); MS: (M+K)⁺ at 436.2 (calc. at 436.5)

3. 2,2',6,6'-Tetracarboxy-4,4'bipyridine (i) 2,2'-6,6'-Tetramethyl-4,4'-bipyridine[23]. 5 g (98 mmol) of a Na dispersion in paraffin was placed in a three-necked flask under nitrogen and treated with 20 mL toluene. The solvent was removed with a syringe and 4.50 g (43 mmol) of 2,6-lutidine in 40 mL dry THF was added. The mixture was stirred until it solidified and was left to stand overnight. Sulfur dioxide was passed over the solid at such a rate as to avoid causing the solvent to boil. $SO_2$ bubbling was stopped after formation of a blue-violet zone on top of the solid mass. The flask was cooled with a mixture of ice/NaCl and then 50 mL of ethanol was added slowly. The reaction mixture was neutralized to pH 7–8 with 10 N NaOH. The organic phase was removed and the aqueous phase was extracted with t-$BuOCH_3$. After evaporation of the solvent a colorless residue was obtained. Yield: 40%. ¹H-NMR (DMSO): δ(ppm) 2.45 (s, br, 12H, $CH_3$); 7.43 (s, 4H, pyridine); ¹³C-NMR (DMSO): 24.4 ($CH_3$); 117.9, 145.7, 158.4 (pyridine)

(ii) 2,2',6,6'-Tetracarboxy-4,4'bipyridine[23]. 2 g (9.4 mmol) of 2,2'-6,6'-tetramethyl-4,4'-bipyridine was dissolved in concentrated sulfuric acid. The solution was cooled to 0° C. and chromium trioxide (11.2 g, 0.11 mol) was added in small portions over a period of 2 hours. The reaction mixture was heated to 75° C. for 2 hours and then transferred to a mixture of ice/water. The expected compound precipitated as a colorless powder and it was removed from the mixture by centrifugation. Yield: 70%. ¹H-NMR (DMSO): δ(ppm) 8.44 (s, 4H, pyridine); 13.5 (s, br, 4H, COOH); MS: (M+Na)⁺ at 355.4 (calc. 355.2).

Preparation of SAM's and Multilayers. Gold slides were purchased from Evaporated Metal Films (EMF). The slides have dimensions of 25 mm×75 mm×1 mm of float glass with cut edges and they are coated with 50 angstroms of chromium followed by 1000 angstroms of gold. The substrates were cut in different sizes according to experimental needs. Slides were immersed in a piranha solution (70% sulfuric acid/30% hydrogen peroxide) at 90° C. for 10–15 minutes in order to provide a clean surface. The slides were rinsed with water, ethanol and dried with nitrogen and used immediately. Monolayers were prepared by immersing the clean gold slides in a 1–2 mM ethanol solution of the desired compound. For pyridine-decanethiol and dodecanethiol the immersion time was 6–8 h. Copper bromide was used as the source of Cu(II) ions (1 mM). Immersion time in copper bromide solutions was 3 h. Subsequent deposition of other organic ligands required 12–24 hours immersion time. The monolayers were rinsed with ethanol, dried with nitrogen and used immediately for experiments.

C. Film Characterization of Films I, II and III (FIGS. 4A–4C)

Conductivity, impedance, contact angle and IR experiments were carried out for SAM I (FIG. 4A) and for films II (FIG. 4B) and III (FIG. 4C) after the addition of each component. The conductivity (CV) results obtained for SAM I in an aqueous solution of $K_3[Fe(CN)_6]$ showed that following deposition of I the conductivity is attenuated significantly compared to bare gold at applied voltages in the range −0.5V to 0.6V versus SCE. This result as well as high impedance values indicate the formation of an ordered monolayer with few major defects, consistent with results obtained previously by Kimura et al. for similar systems.

Conductivity and impedance values for film II change as the individual components are deposited sequentially onto the gold surface. The CV of the bare gold surface shows the redox peaks of the ferricyanide, whereas deposition of the pyridine-capped decanethiol again yields conductivity and impedance values (measured in the range −0.5V–+0.6V versus SCE) that suggest the formation of an ordered insulating monolayer. Similar results were obtained when the ferricyanide was replaced with methyl viologen. After the monolayer was exposed to a solution of Cu(II) ions the CV of the film was nearly identical to that of bare gold with only a small decrease in peak current. There is also a concomitant decrease in impedance. Deposition of the pyrene-containing ligand again results in attenuated conductivity and increased impedance. Similar conductivity and impedance behaviors were obtained for film III upon deposition of the second layer of Cu(II) ions and capping with the pyrene-containing ligand.

Contact Angle Measurements. Contact angle measurements were obtained with a Rame-Hart Model 100-00 Goniometer.

Infrared spectroscopy of SAMs. IR spectra were obtained with a Nexus FT-IR spectrometer equipped with a ThermoNicolet grazing angle accessory and a liquid-nitrogen cooled MCTA detector. The IR beam was incident at 75° on the gold substrates. The optical path was purged with nitrogen gas before and during data acquisition. For each sample 64 scans were collected with a 4 cm-1 resolution (IR with 300 and 500 scans were also collected but no significant change in intensity was observed). The scan range was from 4000 to 1000 cm-1, the detector cut-off is around 800 cm-1. A clean gold substrate was used as background before the acquisition of each samples spectrum.

Contact angle measurements and IR spectra confirm that substantial changes in the surface occur following addition of each layer. The changes in contact angles mirror the changes in hydrophobicity of each of the deposited components while the IR measurements show conclusively the presence of each of the added layers.

Impedance Spectroscopy. The experiments were obtained with a three-electrode setup: the SAM as working electrode, SCE as reference electrode and a Pt wire as auxiliary electrode. The electrolyte solution was 0.1 M $Na_2SO_4$. A 1255-HF frequency response analyzer was used in combination with a EG&G Princeton Applied Research Potentiostat/Galvanostat Model 273. The experiment was carried out at a fixed potential of −0.5 V, frequency range of 100000 to 0.01 Hz, amplitude of 20 mV and collecting 20 points per decade. The working electrode area was kept relatively constant in all experiments at 1 $cm^2$.

Cyclic Voltammetry and Conductivity. All the electrochemistry and photoelectrochemistry experiments were carried out with an EG&G Princeton Applied Research Potentiostat/Galvanostat Model 273. A three-electrode setup was used with the SAM as working electrode, SCE as reference electrode and a Pt wire as the counter electrode. The monolayer was contacted with an alligator clamp and an area of 1 cm$^2$ was always kept immersed in the solution. All solutions were freshly prepared and bubbled with nitrogen for at least 20 minutes before the experiments. The solution used for the experiments was 1 mM potassium ferrocyanide with 50 mM potassium chloride as supporting electrolyte. To limit noise, the electrochemical cell was placed inside a Faraday cage. The cyclic voltammetry curves were obtained in the range −0.5 to +0.7 V, with a scan rate of 50 mV/s and a scan increment of 1 mV.

Photocurrent Measurements. Experiments were carried out with the same experimental setup used for cyclic voltammetry experiments. A 20 mM methyl viologen solution containing 50 mM sodium sulfate as a support was used. The samples were irradiated with a 350 nm Rayonet lamp. The irradiation was through a small slit in the Faraday cage. The cage itself was completely covered in order to eliminate other sources of light. The UV lamp was kept on continuously and a mechanical shutter was used to block exposure of the sample to the light. The sample was typically irradiated at intervals of 20–40 seconds. Individual experiments were performed at a fixed applied potential.

The electrochemical changes that take place with the sequential exposure of the surface to each component in film II and film III indicates that in addition to a possible electronic role, the Cu(II) ion aids in organizing and stabilizing the film, probably by complexing with the pyridyl and bipyridyl ligands present (FIGS. 4A–4C). That deposition of the pyrene-containing ligand in II and III, as well as the bipyridyl ligand in III, results in significantly attenuated current values and enhanced impedance indicates that the deposition of Cu(II) and subsequent addition of ligand results in a specific Cu(II)-ligand interaction rather than a non-specific deposition. If the latter occurred, a significant amount of disorder in the film causing substantial defects and different CV behavior could be expected. In a previous study of metal-legand crytal structures, it has been shown that complexation of Cu(II) by 2,6-pyridinedicarboxylic acid groups results in the formation of stable complexes in which the metal ion is fully encapsulated between two of the ligands (see. J. C. MacDonald et al., *J. Am. Chem. Soc.* 122:11692–11702 (2000).

Figure 5:
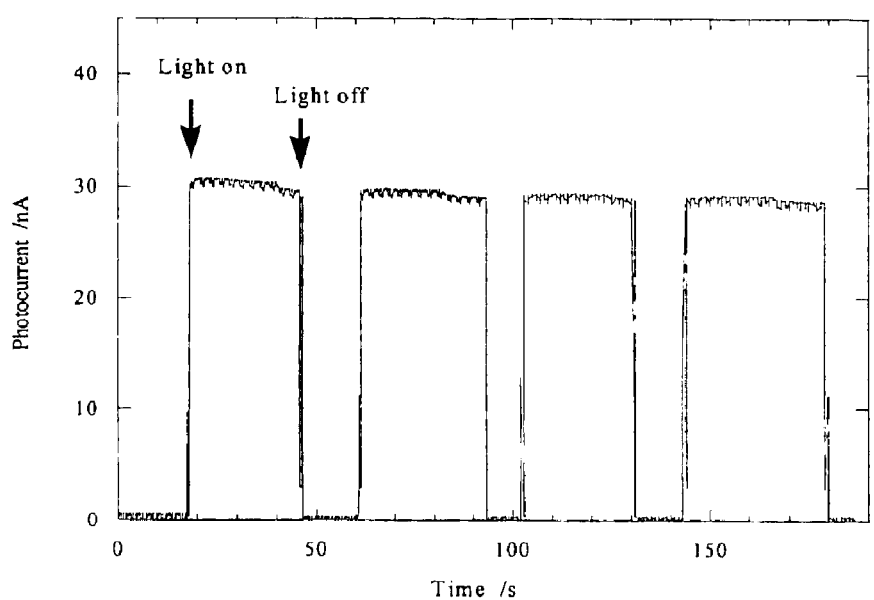
FIG. 5 shows photocurrent ($nA/cm^2$) generated following exposure of III to ~0.1 mW at 350 nm at constant applied voltage=0V vs. SCE for the structure shown in FIG. 4C.

Photoexcitation of SAM I and multilayered films II and III (FIGS. 4A–4C) in the presence of methyl viologen by an unfocused, unfiltered, omnidirectional, 20 W, 350 nm Rayonet lamp, where incident power on the sample was approximately 0.1 mW, causes generation of a cathodic photocurrent in the range 5 nA–30 nA/cm$^2$ with II and III consistently exhibiting higher values than SAM I (5–10 nA/cm$^2$ for SAM I; 10–30 nA/cm$^2$ for II and III). FIG. 5 shows the change in photocurrent for III as a result of alternately shuttering and unshuttering the light source. A photocurrent of 30 nA/cm$^2$ is comparable to, although somewhat smaller than that reported by Imahori and co-workers[7,8] (~50–100 nA/cm$^2$) and represents a quantum efficiency of ~1%. In addition to enhanced current generation, II and III also appear to possess greater stability than SAM I. While repeated photoexcitation of SAM I eventually results in degradation of the film and loss of photocurrent after approximately 10 cycles, II and III did not show any decrease in current over several hours of alternating light/dark cycles.

In the initial film structure evaluations, neither II nor III was an optimized system since there was a mismatch between the spectral output of the excitation lamp and the absorption spectrum of the pyrene chromophore. Subsequent work investigated other complexing ligands and metal ions as well as the effect that the distance of separation between pyrene and the gold surface has on the magnitude of the photocurrent. The initial multilayered film systems range from 2 to 3 nm in distance between pyrene and the surface according to modeling studies. Clearly, the intial studies on simple film systems indicated that the non-covalent assembly approach of the present invention is a potentially efficient and facile means by which to fabricate complex modular multicomponent supramolecular systems for device functions, including conversion of incident light to electric current.

III. Synthesis and Characterization of Complex Film Structures

A. Film Synthesis

Four types of photocurrent generating thin films on a gold surface were fabricated as shown in FIGS. 3A–3D. Films I (FIG. 3A) and II (FIG. 3B) of the present invention which are multilayered systems in which the light absorbing group (e.g. pyrene) is non-covalently coupled to a gold surface via metal-ligand complexation. These two films systems are non-covalently assembled by sequential deposition of three or more components. In film I (FIG. 3A), three components are used: decanethiol linked to a 4-pyridyl-2,6-dicarboxylic acid ligand; either $Cu^{+2}$ of $Co^{+2}$ ions; and a pyridyl-2,6-dicarboxylic acid ligand linked at the 4-position through a methylenyloxy group to the 1-pyrenyl chromophore. Film II (FIG. 3B) possesses two additional non-covalently linked layers: a 4,4'-bipyridyl-2,2'6,6'-tetracarboxylic acid was deposited after either $Cu^{+2}$ or $Co^{+2}$ ions followed by another layer of the same metal ion and finally the pyrene-containing ligand. Films II (FIG. 3C) and IV (FIG. 3D) provided for additional layers which employ different cations for ligand complexing. Details of the synthesis of films I and II are provided in the previous section and below. Synthesis of films II (FIG. 3C) and IV (FIG. 3D) and the method of multilayer film deposition are provided below Most reagents and solvents used in the synthesis of the different units for multilayered assemblies were obtained from Aldrich and were used as received. Chelidamic acid was purchased from Fluka. In experiments using acetone, the solvent was dried over anhydrous sodium sulfate and distilled immediately before the experiment.

The experimental procedure for many of the components of the multilayered systems is provided in section II above. 1,10-(4-methyloxy-pyridine-2,6-dicarboxylic acid)-pyrene was synthesized from pyrene and chelidamic acid following well know literature procedures.

NMR spectra were obtained in an Avance Bruker spectrometer at 400 MHz for proton and 85 MHz for $^{13}$C. Mass spectra were obtained with an LC-MS using the electrospray ionization technique (SynPep Corp. CA). FT-IR were recorded on a Nexus-FT-IR spectrometer using the attenuated total reflectance (ATR) technique.

For multilayer film preparation, gold slides were purchased from Evaporated Metal Films (EMF). The slides have dimensions of 25 mm×75 mm×1 mm of float glass with cut edges and they are coated with 50 angstroms of chromium followed by 1000 angstroms of gold. The substrates were cut in different sizes according to experimental needs. Slides were immersed in a piranha solution (70% sulfuric acid/30% hydrogen peroxide) at 90° C. for 10–15 minutes in order to provide a clean surface. The slides were rinsed with water, ethanol and dried with nitrogen and used immediately. Monolayers were prepared by immersing the clean gold slides in a 1–2 mM ethanol solution of the desired compound. For pyridine-decanethiol the immersion time was 6–8 h. Copper bromide and iron bromide were used as the source of Cu(II) and Fe(III) ions in 1 mM solutions in ethanol. Immersion time for both solutions was less than 3 h. Cobalt bromide and cobalt chloride were used in 1 mM solutions in ethanol and acetone with immersion times of 24 h. Subsequent deposition of other organic ligands (bypyridine, pyrene-pyridine, disubstituted pyrene) required 12–30 hours immersion time and was obtained from 1 mM solutions in ethanol or methanol. The films were rinsed with ethanol and dried with nitrogen before changing from one solution to the next one in order to avoid the presence of physically adsorbed molecules on the surface.

Thin film mulilayer photocurrent-generating systems were successfully fabricated as the structures shown in FIGS. 3A–3D using $Cu^{+2}$, $Fe^{+3}$ and $Co^{+2}$ as metal ions for complexation with modified pyridine ligands. CA, IR, CV and IS were used as analytical tools to study the sequential deposition of each layer. Systems with $Ni^{+2}$, $Zn^{+2}$ and $Mn^{+2}$ did not appear to give complete surface coverage as exhibited by the small changes in CV graphs and the lack of photocurrent generation.

B. Film Characterization

Figure 6:
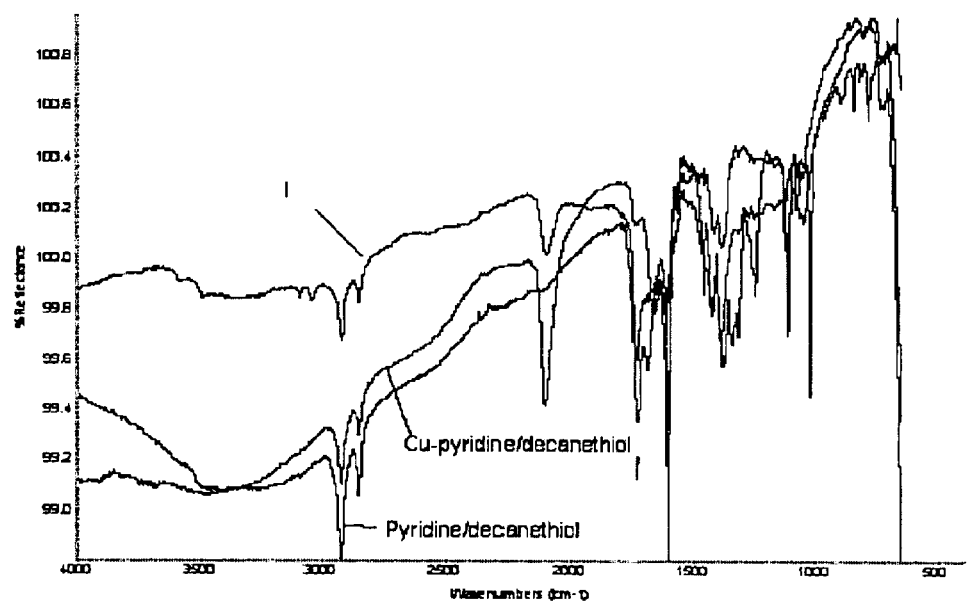
FIG. 6 shows a typical IR spectra after deposition of each layer of Film I ($M=Cu^{+2}$) shown in FIG. 3A.

Contact Angle. Contact angle measurements were obtained with a Rame-Hart Model 100-00 Goniometer. Drops of water (2 uL) were deposited with a micropipette and the sessile drop contact angle was measured. The average of at least three measurements for each sample was obtained. The sessile drop contact angle technique measurements reflected the changes in hydrophilicity/hydrophobicity of the films with sequential deposition of each layer. The results for all multilayers confirmed the sequential deposition of each layer Grazing angle Fourier Transform Infrared Spectroscopy (FTIR). IR spectra were obtained with a Nexus FT-IR spectrometer equipped with a ThermoNicolet grazing angle accessory and a liquid-nitrogen cooled MCTA detector. The IR beam was incident at 75° on the gold substrates. The optical path was purged with nitrogen gas before and during data acquisition. For each sample 64 scans were collected with a 4 $cm^{-1}$ resolution. IR spectra with 300 and 500 scans were also collected but no significant change in intensity was observed. The scan range was from 4000 to 1000 $cm^{-1}$, the detector cut-off is close to 800 $cm^{-1}$. A clean gold substrate was used as background before the acquisition of each samples spectrum. IR spectra showed substantial changes after deposition of each layer. FIG. 6 shows a typical IR measurement for various film layers with Film I (FIG. 3A). With deposition of each metal ion, the vibrational changes in the carboxylic acid units of the pyridine ligand were monitored. With films III and IV a decrease in absorption intensity was found as the number of layers increased, because sensitivity of the technique does not allow measuring inner layers leaving only small absorption bands of the aromatic units (pyrene and pyridine).

Cyclic Voltammetry The electrochemical experiments were obtained with an EG&G Princeton Applied Research Potentiostat/Galvanostat Model 273. A three-electrode setup was used with the SAM as working electrode, SCE as reference electrode and a Pt wire as the counter electrode. The monolayer was contacted with an alligator clamp and an area of 1 $cm^2$ was always kept immersed in the solution. All solutions were freshly prepared and bubbled with nitrogen for at least 20 minutes before the experiments. The electrolyte solution was 1 mM potassium ferrocyanide with 50 mM potassium chloride. To limit noise, the electrochemical cell was placed inside a Faraday cage. The cyclic voltammetry curves were obtained in the range –0.5 to +0.7 V with a scan rate of 50 mV/s and a scan increment of 1 mV. Cyclic voltammetry experiments were also obtained with a 1 M NaCl solution, with scan rates between 10–50 mV/s, and scan increment of 1 mV.

Typically, deposition of the first film layer always gives a high insulating surface as it is expected from alkanethiols assembled on gold. Deposition of the metal ion again produces a conductive surface as is shown by with the CV curves measured for the redox process of the ferryciamide in solution. With $Fe^{+3}$ and $Cu^{+2}$ the results show a behavior similar to bare gold substrates, proving a complete coverage of the surface. With $Co^{+2}$, the coverage is not complete as shown by a poorly resolved pattern of the CV curve. With all other metals, immersion of the substrate for extended periods of time did not improve the conductivity of the surface. The best results were obtained for $Zn^{+2}$, which shows a conductivity of about ⅓ of bare gold after immersion of the substrate in a 1 mM $ZnBr_2$ solution in DMSO for 5 days. For all systems deposition of a third layer (pyrene-pyridine or bypyridine ligands) shows again a decrease in conductivity although not as high as with the first layer. The small length of additional ligands (compared to the first layer) and the intermediate layers of metal ions do not allow for perfect insulation. The low electronic insulating properties of the films as the number of layer increases made difficult to use CV to characterize Films III and IV.

Cyclic voltammetry was also used to measure the reduction potential of the metals in the multilayer. The results were satisfactory only for $Cu^{+2}$; its reduction potential was determined at +0.2±0.1 V using a 1 M NaCl electrolyte solution. The redox current shows a linear relationship with scan rate in the range 5–50 mV/s, and the reproducibility of the oxidation peaks is maintained for a number of scans (~15). Therefore the complex in the multilayer is a quasi-reversible unit, although not as well behaved as reported for other systems, for example Rh complexes (C. Lin et al., *J. Am. Chem. Soc.* 125:336–337 (2003)).

The redox potentials of $Co^{+2}$ and $Fe^{+3}$ were not possible to detect, either with an aqueous solution or an organic electrolyte solution (0.1 tetrabutylammonium perchlorate in acetonitrile or THF). Other groups have encountered problems with detection of redox peaks for metals in monolayers or multilayers[28,29]. Possible explanations for this problem are that it might not be likely to monitor the redox properties of a complex in a monolayer because: (1) the monolayer is not electrochemically stable, destruction of the monolayer might occur before any reversible electrochemical process; (2) there is a bad packing of the different layers in the film, which can spread out the redox potentials making them not detectable.

Impedance spectroscopy: Experiments were carried out with the same three-electrode setup used for cyclic voltammetry. The electrolyte solution was 0.1 M $Na_2SO_4$. A 1255-HF frequency response analyzer was used in combination with the EG&G Princeton Applied Research Potentiostat/Galvanostat. The experiment was carried out at a fixed potential of –0.5 V, frequency range of 100000 to 0.1 Hz, amplitude of 20 mV and collecting 20 points per decade. The working electrode area was kept relatively constant in all experiments at 1 $cm^2$. The impedance data was plotted as Nyquist and Bode plots, and analyzed using the LEVMRUN software package for complex-non least squares calculations (CNLS). The multilayer films show the characteristic behavior observed with other monolayer and multilayer films that have been reported before. Impedance results for Pyridine-decanethiol (first layer) showed the same pattern for typical alkanethiols adsorbed on gold as described by Lennox et al. (*J. Phys. Chem B* 104:9004–9010 (2000); *Langmuir* 16:4222–4228, 7464–7470 (2000)). The monolayer is almost defect-free between +0.4 to −0.2 V, and the results can be interpreted using the Helmholtz capacitor model. At lower potentials the Helmholtz model does not longer fit the results, and a Randles circuit is used (a solution resistance in series with a parallel combination of monolayer capacitance and resistance). Similar results were observed with sequential addition of the multilayer components.

A potential of −0.5 V was chosen to carry out all measurements as modeling of the impedance result using a Randles circuit allows to track changes in the film according to changes in the multilayer's resistance. $R_{SAM}$ decreases with deposition of any metal (in a similar way as reported by Reinhoudt[28] for monolayers complexed with $Ni^{+2}$ and $Co^{+2}$). Alternate changes in $R_{SAM}$ are observed with deposition of following layers.

Monolayers with high impedance barrier show $R_{ct}$ values of $1 \times 10^5$ ohms/cm$^2$ and capacitance of the order of 1–5 uF/cm$^2$. Films I–IV showed similar values with deposition of the pyridine-decanethiol layer, confirming the formation of a well-packed, relatively free of defects monolayer. The order of the film seems to decrease as the number of layers increases as capacitance values were calculated between 8–24 uF/cm$^2$ after deposition of the first metal layer. The results show better deposition of copper layers compared to cobalt and iron.

Photocurrent experiments. Experiments were carried out with the same experimental setup used for cyclic voltammetry experiments. A 20 mM methyl viologen and a 20 mM EDTA solution, both containing 50 mM sodium sulfate as supporting electrolyte were used. The samples were irradiated with a 350 nm Rayonet lamp. The irradiation was through a small slit in the Faraday cage. The cage itself was completely covered in order to eliminate other sources of light. The UV lamp was kept on continuously and a mechanical shutter was used to block exposure of the sample to the light. The sample was typically irradiated at intervals of 20–40 seconds. Experiments were obtained at different fixed applied potentials, from −0.3 to +0.5 V.

Photocurrent measurments of films I–IV (FIGS. 3A–3D) are provided in Table 1 where current is given in nA/cm$^2$, positive values indicate cathodic current and negative values indicate for anodic current. In Table I, the notation employed is as follows:

Pyrdt: pyridine-decanethiol
Py: pyrene-pyridine
By: bypyridine
Pyr: pyridine-pyrene-pyridine
Pydpa: pyrene substitution in 2 position by DPA.

UV-exposure of all films in the presence of methyl viologen or EDTA exhibited similar results. Exposure of films without pyrene yield a very low intensity dark current, with no changes when light was illuminating the sample. The dark current is high only at negative potentials lower than −0.3 V. Photocurrent of systems with pyrene was not determined at these potentials because of the intensity of dark current.

Cathodic photocurrent is generated at applied potentials below +0.2 V in the presence of methyl viologen. After UV absorption, the excited state of pyrene transfers an electron to methyl viologen or oxygen in solution. These electron carriers diffuse and transfer the electron to the counter electrode generating the photocurrent. The ground state of pyrene is generated by electron injection from the gold surface. The presence of the metal ion (with redox potentials between 0 and 1.0 V) probably enhances the electron transfer by providing electron hops between the gold surface and pyrene. An increase in photocurrent with more negative potentials confirms that the current is cathodic, as the rate of electron donation from the gold to the pyrene affects the generation of current. With a solution of only supporting electrolyte the photocurrent is generally very low and probably oxygen is acting as the electron carrier.

TABLE 1

Photocurrent Results for Films I–IV (FIG. 3A–3D)

| Potential (Volts) | MV | EDTA |
|---|---|---|
| Film I: Py-Cu-Pyrdt | | |
| −0.3 | +44 | +78 |
| −0.2 | +28 | +63 |
| −0.1 | +18 | +42 |
| 0 | +14 | +30 |
| +0.1 | +1.5 | +10 |
| +0.2 | +1.6 | +10 |
| +0.3 | −10 | +1 |
| +0.4 | −12 | −9 |
| +0.5 | −9 | −9 |
| Film I: Py-Co-Pyrdt | | |
| −0.3 | +100 | +100 |
| −0.2 | +40 | +100 |
| −0.1 | +15 | +75 |
| 0 | +7 | +50 |
| +0.1 | +3 | +10 |
| +0.2 | −1.5 | +19 |
| +0.3 | −4 | +4 |
| +0.4 | −5 | −5 |
| +0.5 | −5 | −15 |
| Film I: Py-Fe-Pyrdt | | |
| −0.3 | +10 | +52 |
| −0.2 | +31 | +48 |
| −0.1 | +7 | +18 |
| 0 | +6 | +20 |
| +0.1 | −14 | −2 |
| +0.2 | −21 | −3 |
| +0.3 | −22 | −4 |
| +0.4 | −24 | −10 |
| +0.5 | −22 | −29 |
| Film II: Py-Cu-By-Cu-Pyrdt | | |
| −0.2 | +22 | +34 |
| −0.1 | +22 | +13 |
| 0 | +28 | +7 |
| +0.1 | +6 | +4 |
| +0.2 | −4.6 | −2.2 |
| +0.3 | −6.2 | −4.5 |
| +0.4 | −3.8 | −11.7 |
| +0.5 | −2.4 | −12.6 |
| Film II: Py-Co-By-Co-Pyrdt | | |
| −0.2 | +1 | +3.5 |
| −0.1 | +0.35 | +1.8 |
| 0 | −0.7 | +0.5 |
| +0.1 | −1.1 | −0.5 |
| +0.2 | −1.5 | −1.7 |
| +0.3 | −1.7 | −2.9 |
| +0.4 | −3 | −3.5 |
| +0.5 | −3.1 | −4.7 |
| Film II: Py-Fe-By-Fe-Pyrdt | | |
| −0.2 | −10 | +10 |
| −0.1 | −15.1 | +11.8 |
| 0 | −17.5 | +7.65 |
| +0.1 | −19.7 | −2 |
| +0.2 | −22.3 | −6 |

TABLE 1-continued

Photocurrent Results for Films I–IV (FIG. 3A–3D)

| Potential (Volts) | MV | EDTA |
|---|---|---|
| +0.3 | −22.9 | −6 |
| +0.4 | −16.7 | −17.7 |
| +0.5 | −19.2 | −12.7 |
| Film III: Py-Cu-Pydpa-Cu-Pyrdt | | |
| −0.3 | — | +26 |
| −0.2 | +21.5 | +70 |
| −0.1 | +17 | +60 |
| 0 | +10 | +42 |
| +0.1 | +7 | +31.5 |
| +0.2 | −2.4 | +10.4 |
| +0.3 | −2.7 | −1.4 |
| +0.4 | −9.5 | −12.5 |
| +0.5 | −7 | −9.7 |
| +0.6 | −4 | −13 |
| Film III: Py-Co-Pydpa-Co-Pyrdt | | |
| −0.2 | −0.1 | +10 |
| −0.1 | −1.2 | +14.6 |
| 0 | −1.9 | +8.9 |
| +0.1 | −0.6 | +4.7 |
| +0.2 | −1.5 | +1.1 |
| +0.3 | −2.2 | −2.8 |
| +0.4 | −3.5 | −4.6 |
| +0.5 | −3.7 | −6.2 |
| Film III: Py-Fe-Pydpa-Fe-Pyrdt | | |
| −0.2 | −4.2 | +23.3 |
| −0.1 | −8 | +29.6 |
| 0 | −15.4 | +6.25 |
| +0.1 | −10.4 | −4 |
| +0.2 | −26.4 | −10 |
| +0.3 | −18 | −14.1 |
| +0.4 | −20.6 | −17.9 |
| +0.5 | −33.7 | −20.3 |
| Film IV: Py-Cu-Pydpa-Cu-Pydpa-Cu-Pyrdt | | |
| −0.3 | +30 | +192.5 |
| −0.2 | +62 | +190 |
| −0.1 | +29 | +123 |
| 0 | +12 | +75 |
| +0.1 | 0 | +68 |
| +0.2 | −3 | +25.4 |
| +0.3 | −6.3 | −6.2 |
| +0.4 | −15.7 | −21.5 |
| +0.5 | −16.6 | −24.9 |
| +0.6 | −20 | −33 |
| Film IV: Py-Co-Pydpa-Co-Pydpa-Co-Pyrdt | | |
| −0.2 | −3.3 | +5.5 |
| −0.1 | −2.2 | +8.8 |
| 0 | −4.3 | +2.25 |
| +0.1 | −2.4 | +1.25 |
| +0.2 | −1.8 | 0 |
| +0.3 | −3.4 | −1.4 |
| +0.4 | −4.0 | −3.5 |
| +0.5 | −4.7 | −3.6 |
| Film IV: Py-Fe-Pydpa-Fe-Pydpa-Fe-Pyrdt | | |
| −0.2 | −7 | +16 |
| −0.1 | −7.8 | +24 |
| 0 | −14.7 | +6.5 |
| +0.1 | −14 | −6.9 |
| +0.2 | −13.6 | −20.1 |
| +0.3 | −24.6 | −29.8 |
| +0.4 | −29.6 | −45.3 |
| +0.5 | −31 | −48.1 |

The current obtained with all films is stable for extended periods of time, and reproducible (intensity generally within less than 20% deviation). This photocurrent stability is dependent on the good formation of a multilayer, but also on the length of the spacer from the gold to the first metal layer.

We have fabricated films similar to I and II using a propanethiol linker to the gold surface. However an unstable current was obtained as the small distance between gold and pyrene increases the rate of back electron transfer towards the gold surface as has been observed previously.

With Film I (M=$Cu^{+2}$), when the applied potential is higher than +0.2 V an anodic photocurrent was measured. This current does not increase significantly with more positive potentials. The mechanism of anodic photocurrent in the presence of methyl viologen is not well understood as there is no chemical species in solution with the proper redox potential to regenerate the ground state of pyrene. A similar result was obtained when only supporting electrolyte was present in the solution.

Photocurrent experiments were carried out in the presence of EDTA as sacrificial electron donor. EDTA exhibited the same behavior as MV. An anodic photocurrent was measured at $V_{appl}$>0.2 V (which could be consistent with the mechanism of FIG. 12), but the intensity of the current is very similar to the values measured with methyl viologen and sodium sulfate. Most importantly a cathodic current was detected at $V_{appl}$≦+0.2 V. This cathodic current is generally higher (3–4 times) than with methyl viologen solution. We have no clear explanation for this surprising result. There are no electron carriers in solution other than oxygen and $H^+$ but it is not expected to obtain higher current than in the presence of a good electron carrier as MV. To further understand these results we measure photocurrent of I ($Cu^{+2}$) using DABCO as sacrificial electron donor. We expected to obtain higher anodic current at positive potentials. However a very low current (~5 $nA/cm^2$) was measured at positive potentials. Cathodic photocurrent was measured at −0.2 V but its low intensity (<5 $nA/cm^2$) assure us that it is result of having oxygen and $H^+$ as electron carriers.

Based on the above observations it appears that anodic photocurrent is not a significant process for film systems I–IV as its intensity does not increase significantly with positive potentials or with different electrolytes. Cathodic photocurrent is generated with significant intensity and stability, the remaining factor is to explain the higher current intensity measured with EDTA solution than with methyl viologen.

Films I with $Co^{+2}$ and $Fe^{+3}$ gave similar results as with $Cu^{+2}$, and the film with $Co^{+2}$ generated the highest current values using EDTA. For all films, current changes from aniodic to cathodic at potentials of +0.1 or 0 V. Only anodic photocurrent was observed with methyl viologen for some films with Fe.

Incorporation of a bypyridine ligand in the multilayer increased the magnitude of the photocurrent (Film II gave a current ~50% higher than I at 0 V), probably because of the larger separation between pyrene and gold and because electron transfer is favored by electron hops through the metal layers. Incorporated of more than one pyrene in the multilayer (III and IV) further increased the intensity of the cathodic photocurrent. The increase of generated photocurrent on these films is greater than film II, as expected by increasing the number of pyrene units on the film. Although generation of more current is an encouraging result, the major drawback is that the order and stability of the multilayer seems to decrease with an increase of the number of layers (based on electrochemical characterization). Improvement of the photocurrent generation is also better for multilayers with Cu than with Fe and Co (see tables of photocurrent data). We might be able to improve generation of photocurrent from these type of non-covalent assembled films by choosing slightly different ligands, that can provide a better complexation with different metals and rigidity to the system in order to build larger multilayered films. We are also interested in extending our results by incorporating chromophores with extinction coefficients higher than the one for pyrene and with strong absorption in the visible region, in order to make more efficient and useful devices.

Having described the preferred embodiments of the invention, it will now become apparent to one of skill in the art that other embodiments incorporating the disclosed concepts may be used. Therefore, it is not intended to limit the invention to the disclosed embodiments but rather the invention should be limited only by the spirit and scope of the following claims.

What is claimed is:

1. A self-assembled monolayer for coupling to a surface having the following general formula:

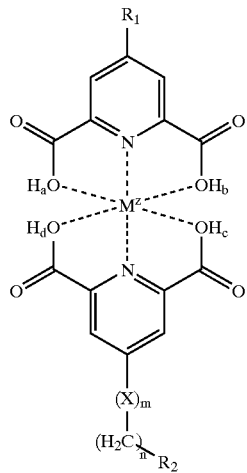

where $R_1$ is a chromophore, a photooxidant, a photoreductant, a functional group comprising 2,6-pyridinedicarboxylate ligands or a 2,6-pyridinedicarboxylate ligand structure for attaching additional film layers;

where M is a transition metal ion, a lanthanide metal ion or an ion that forms charge neutral complexes with 2,6-pyridinedicarboxylate ligands;

where Z is a positive integer between 1 and 4;

where a,b,c, and d are either 0 or 1 and $(a+b+c+d)=(4-Z)$;

where X is oxygen, nitrogen, sulfur or an atom other than carbon;

where m is 0 or 1;

where n is an integer between 0 and 20; and where $R_2$ is sulfur, silicon or a surface coupling group.

2. A multilayer thin film structure for coupling to a surface having the following general formula

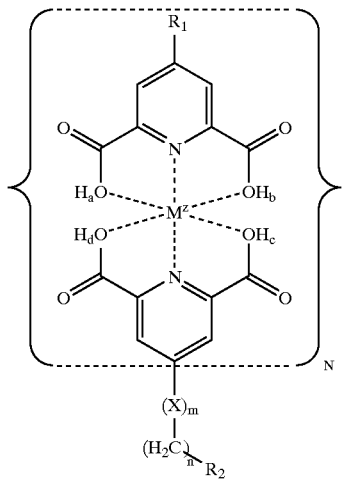

where R1 is a chromophore, a photooxidant, a photoreductant, a functional group comprising 2,6-pyridinedicarboxylate ligands or a 2,6-pyridinedicarboxylate ligand structure for attaching additional film layers;

where M is a transition metal ion, a lanthanide metal ion or an ion that forms charge neutral complexes with 2,6-pyridinedicarboxylate ligands;

where Z is a positive integer between 1 and 4;

where a,b,c, and d are either 0 or 1 and $(a+b+c+d)=(4-Z)$;

where N is a positive integer greater than 1;

where X is oxygen, nitrogen, sulfur or an atom other than carbon;

where m is 0 or 1;

where n is an integer between 0 and 20; and where R2 is sulfur, silicon or a surface coupling group.

* * * * *